US008383415B2

(12) United States Patent
Ayi et al.

(10) Patent No.: US 8,383,415 B2
(45) Date of Patent: Feb. 26, 2013

(54) HYDROGEL COMPOSITION TO ENHANCE FLUORESCENCE

(75) Inventors: Teck Choon Ayi, Singapore (SG); Mei-Mei Jill Tong, Singapore (SG); Vee Sin Peter Lee, Singapore (SG)

(73) Assignee: DSO National Laboratories, Singapore (SG)

( * ) Notice: Subject to any disclaimer, the term of this patent is extended or adjusted under 35 U.S.C. 154(b) by 477 days.

(21) Appl. No.: 12/083,593

(22) PCT Filed: Oct. 13, 2005

(86) PCT No.: PCT/SG2005/000353
§ 371 (c)(1),
(2), (4) Date: Nov. 21, 2008

(87) PCT Pub. No.: WO2007/043973
PCT Pub. Date: Apr. 19, 2007

(65) Prior Publication Data
US 2009/0130773 A1    May 21, 2009

(51) Int. Cl.
G01N 21/76    (2006.01)
(52) U.S. Cl. .......... 436/172; 436/86; 436/164; 424/484; 424/486; 424/488; 424/499
(58) Field of Classification Search ........................ None
See application file for complete search history.

(56) References Cited

U.S. PATENT DOCUMENTS

| | | | |
|---|---|---|---|
| 5,069,908 A | 12/1991 | Henley | |
| 5,750,585 A | 5/1998 | Park et al. | |
| 5,863,551 A | 1/1999 | Woerly | |
| 6,005,161 A | 12/1999 | Brekke et al. | |
| 6,497,903 B1 | 12/2002 | Hennink et al. | |
| 2002/0160400 A1 | 10/2002 | Lakowicz | |
| 2003/0138490 A1 | 7/2003 | Hu et al. | |
| 2006/0269590 A1 | 11/2006 | Trotter et al. | |

OTHER PUBLICATIONS

Xu, Shengqing, et al. From hybrid microgels to photonic crystals, 2003, Advanced Functional Materials, vol. 13(6), pp. 468-472.*
Yin, Yihua, et al. Hydrogels for colon-specific drug delivery: Swelling kinetics and mechanism of degrsdation in vitro, 2001, Journal of Polymer Science: Part B: Polymer Physics, vol. 39, pp. 3128-3137.*
D'Urso, E. M., et al., New hydrogel based on polyethylene glycol cross-linked with bovine serum albumin, 1994, Biotechlology Techniques, vol. 8(2), pp. 71-76.*
Voytas D., *Resolution and Recovery of Large DNA Fragments*, Current Protocols in Molecular Biology. Edited by Ausubel, F.M. et al (2000), 2.5.1-2.5.9.
Li, J. et al, *Highly Photoluminescent CdTe/Poly(N-isopropylacrylamide) Temperature-sensitive Gels*, Advanced Materials (2005) 17(2), 163-165.
Horie, K. et al, *Dansyl Fluorescence and Local Structure of Dansyl-labelled Core-shell and Core-hair Type Microspheres in Solution*, Macromolecular Chemistry and Physics (2003) 204, 131-138.
Subr, V. et al, *Release of Macromolecules and Daunomycin from Hydrophillic Gels Containing Enzymatically Degradable Bonds*, Journal of Biomaterials Science (1990) 1(4), 261-278.
Dong L. C. et al, *Dextran Permeation through Poly(isopropylacrylamide) Hydrogels*, Jounrla of Biomaterials Science, Polymer edition (1994) 5(5), 473-484.

(Continued)

*Primary Examiner* — Robert Xu

(57) ABSTRACT

A composition comprising a hydrogel particle and a fluorophore; wherein said composition produces an enhanced fluorescent signal when excited by an energy source capable of exciting the fluorophore.

25 Claims, 17 Drawing Sheets

OTHER PUBLICATIONS

Choi S. H. et al, *Galactosylated Poly(N-isopropYlactylamide) Hydrogel Submicrometer Particles for Specific Cellular Uptake within Hepatocytes*, Journal of Colloidal and Interface Science (2002) 251, 57-63.

Flint, N. J. et al, *Fluroscence Studies of the Thermoresponsive Behaviour of Aqueous Dispersions of Microgels based on Poly(Nisopropylactylamide)*, ACS Symposium Series (2001) 780, 208-222.

Zhang, X-X et al, *Determination of Morphine by Capillary Electrophoresis Immunoassay in Thermally Reversible Hydrogel-modified Buffer and Laser-induced Fluorescence Detection*, Journal of Chromatography A (2000) 895, 1-7.

Wang, Y-C. et al, *A Phase Separation Fluoroimmunoassay of Estradiol*, Chinese Journal of Chemistry (2001) 19, 1205-1210.

Benson et al, *Heterodimeric DNA-binding dyes Designed for Energy Transfer: Stability and Applications of the DNA Complexes*, Nucleic Acid Research (1993) 21, 5720-5726.

Guney, O., *Multiple-point Adsorption of Terbium Ions by Lead Ion Templated Thermosensitive Gel: Elucidating Recognition of Conformation in Gel by Terbium Probe*, Journal of Molecular Recognition (2003) 16, 67-71.

Benson et al, *Fluorescence Energy-transfer Cyanine Heterodimers with High Affinity for Double-stranded DNA*, Analytical Biochemistry (1995) 231, 247-255.

Smith et al, *Fluorescence Detection in Automated DNA Sequence Analysis*, Nature (1986) 321, 674-679.

Prober et al, *A System for Rapid DNA Sequencing with Fluorescent Chain-terminating Dideoxynucleotides*, Science (1987) 238, 336-343.

Li et al, *Design, Synthesis, and Spectroscopic Properties of Peptide-Bridged Fluorescence Energy-Transfer Cassettes*, Bioconjugate Chemistry (1999) 10, 241-245.

Denijn et al, In-Situ *Hybridization: A Valuable Tool in Diagnostic Pathology*, Acta Pathologica, Microbiologica et Immunologica Scandinavica (1992) 100, 669-681.

Wiegant et al, *Differentially Painting Human Chromosome Arms with Combined Binary Ratio-labeling fluorescence* In Situ *Hybridization*, Genome Research (2000) 10, 861-865.

Lipshutz et al, *High Density Synthetic Oligonucleotide Arrays*, Nature Genetics Supplement (1999) 1, 20-24.

Ferea et al, *Observing the living genome*, Current Opinion in Genetics & Development (1999) 9, 715-722.

Kim and Lee (2004) Polymeric Materials: Science and Engineering, 90, 637-638.

Dingenouts et al, *Observation of the Volume Transition in Thermosensitive Core-Shell Latex Particles by Small-Angle X-ray Scattering*, Macromolecules (1998) 31, 8912-8917.

Lawandy et al, *Laser Action in Strongly Scattering Media*, Nature (1994) 368, 436-438.

Cao, *Random Laser Development, Features and Applications*, Optics & Photonics News (2005) 16, 24-29.

Kim and Healy et al, *Synthesis and Characterization of Injectable Poly(N-isopropylacrylamide-co-acrylic acid) Hydrogels with Proteolytically Degradable Cross-Links*, Biomacromolecules (2003) 4, 1214-1223.

Van Djik-Wolthuis et al, *Synthesis, Characterization, and Polymerization of Glycidyl Methacrylate Derivatized Dextran*, Macromolecules (1995) 28, 6317-6322.

De Smedt et al, *Characterization of the Network Structure of Dextran Glycidyl Methacrylate Hydrogels by Studying the Rheological and Swelling Behaviour*, Macromolecules (1995) 28, 5082-5088.

Huang et al, *Controlled drug release from hydrogel nanoparticle networks*, Jounal of Control Release (2004) 94, 303-311.

Klonis et al, *Effect of Solvent—Water Mixtures on the Prototropic Equilibria of fluorescein and on the Spectral Properties of the Monoanion*, Photochemistry & Photobiology (2000) 72, 179-185.

Klonis et al, *Spectral Properties of Fluorescein in Solvent-Water Mixtures: Applications as a Probe of Hydrogen Bonding Environments in Biological Systems*, Photochemistry & Photobiology (1998) 67, 500-510.

Martin, *Hydrogen Bond Effects on Radmtionless Electrqnlc Transitions in Xanthene Dyes*, Chemical Physics Letters (1975) 35, 105-111.

\* cited by examiner

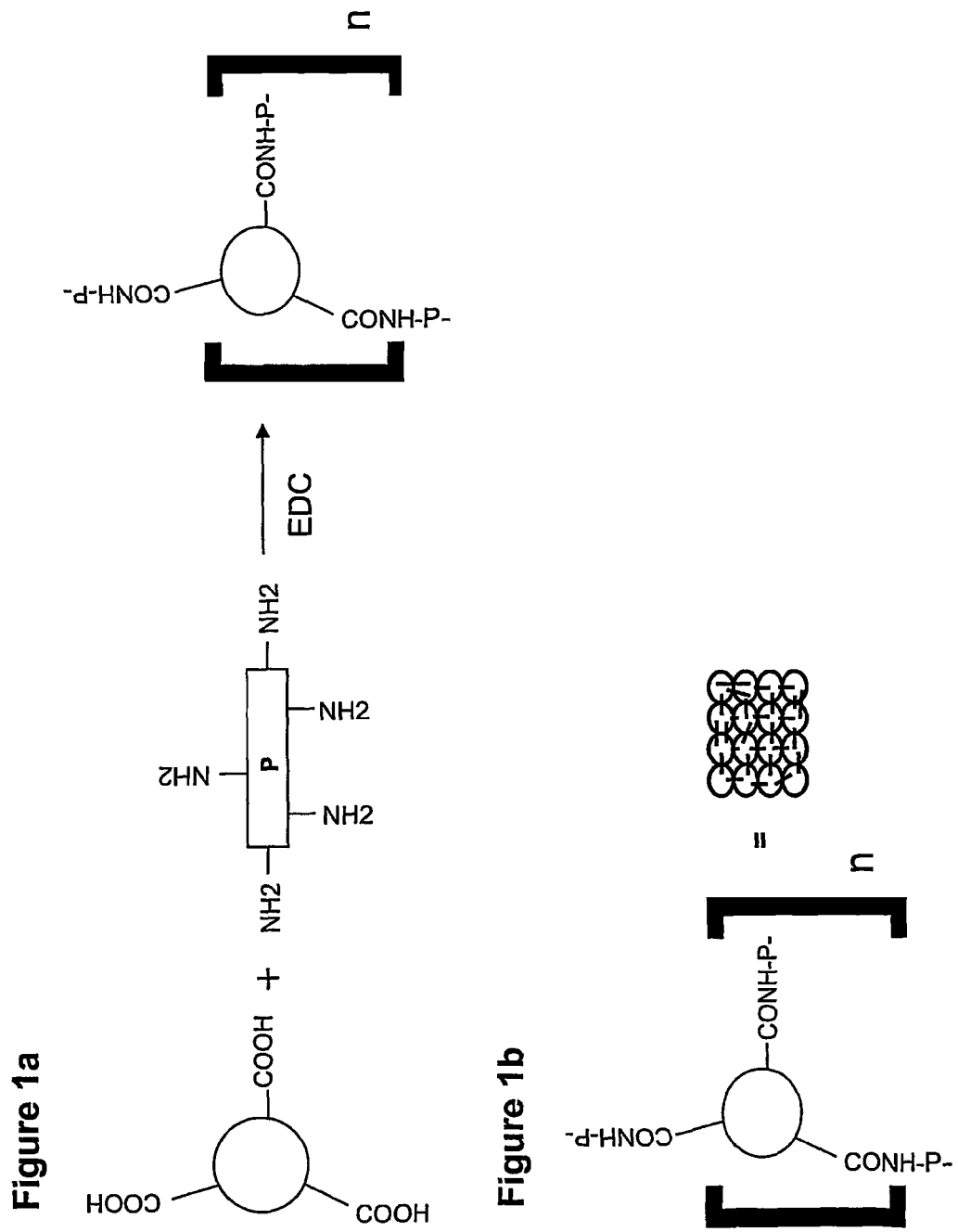

Loading by diffusion of dye into material

Digestion of crosslinking protein or peptide substrate

Release of reporter dye and enhancement of fluorescence

— Fluorescent reporter dye
— Targeted protease

HYDROGEL COMPOSITION TO ENHANCE FLUORESCENCE

PRIORITY CLAIM

This is a U.S. national stage of application No. PCT/SG2005/000353, filed on Oct. 13, 2005.

FIELD OF THE INVENTION

The present invention relates to compositions and methods for increasing and detecting the fluorescence of fluorescent and non-fluorescent compounds, including biomolecules. The present invention also relates to methods for detecting the presence of compounds, including biomolecules.

BACKGROUND ART

In recent years fluorescence has become a dominant technology in fields such as environmental monitoring, biotechnology (eg drug discovery and cellular imaging) and medicine (eg medical testing and imaging). The greatly enhanced ability to detect specific molecules has also led to rapid advancements in diagnostics. For example, fluorescence detection is widely used in medical testing and DNA analysis because of the high degree of sensitivity obtained using fluorescent techniques. Small numbers of molecules can be detected using fluorescence technology.

Most of the knowledge about fluorescence is based on measurements of the spectroscopic properties of fluorophores that upon excitation, radiate into a homogeneous and non-conducting medium, typically referred to as free space. A fluorophore is like an antenna, which oscillates at high frequency and radiates short wavelengths. Local effects are not usually observed because of the small size of fluorophores relative to the experimental apparatus.

Some of the fluorescence techniques used to detect the presence of molecules include Resonance Energy Transfer (RET), immunofluorescent assays, and fluorescence in situ hybridization. Detection of the molecule of interest is generally limited by the properties of the fluorophore used.

One well-known detection method is Surface Enhanced Raman Scattering (SERS). It is known that the presence of a metallic surface can enhance the Raman signals by factors of $10^3$ to $10^8$ and reports of even larger enhancements have appeared. The presence of a nearby metal film, island or particle can also alter the emission properties of fluorophores.

SERS has been observed for many types of molecules absorbed on the surface of certain metals, such as gold, silver and copper. Similarly, fluorescence signal can also be enhanced many-fold when fluorophores were placed in close proximity to silver particle coated surfaces and silver island films. Enhancement is believed to be due to the interaction of the raman and fluorescence signals with surface plasmon on a metal surface, although the exact mechanisms are not clearly understood. U.S. Ser. No. 10/073,625, which is incorporated by reference in its entirety, discloses compositions and methods for increasing fluorescence intensity of molecules by using metal particles and biomolecules positioned at a distance apart sufficient to adjust intrinsic emission of electromagnetic radiation from the biomolecule in response to an amount of exciting electromagnetic radiation.

Many molecules are not themselves fluorescent. Typically in this case, extrinsic fluorophores are added covalently or non-covalently to allow molecules that do not ordinarily fluoresce or do not fluoresce at useful levels to be detected. However, in some cases, labelling a molecule with an extrinsic fluorophore can alter the activity of the molecule, potentially creating experimental artefacts. For example, labelling a biomolecule may alter the biomolecule such that it loses its biological activity. Problems with current fluorescent techniques stem in part from the low fluorescent intensities of commonly used fluorophores. Additionally, background fluorescence can be significant when using the low wavelength excitation radiation required by some fluorophores or when large quantities of fluorophore are required.

DNA, a biomolecule of great interest to many researchers, ordinarily does not fluoresce at detectable levels. As a result, extrinsic fluorophores are often added to DNA to facilitate the detection of DNA on gels (Benson et al. (1993) Nucleic Acids Res. 21, 5720-5726; Benson et al. (1995) Analytical. Biochem. 231, 247-255), in DNA sequencing (Smith et al. (1986) Nature 321, 674-679; Prober et al. (1987) Science 238, 336-343; Li et al. (1999) Bioconjugate Chem. 10, 241-245), in fluorescence in-situ hybridization (Denijn et al. (1992) APMIS 100, 669-681; Wiegant et al. (2000) Genome Res. 10, 861-865), and for reading of DNA arrays for gene expression (Lipshutz et al. (1999) Nat. Genet. SuppL. 1, 20-24; Ferea et al. (1999) Curr. Opin. Genet. Dev. 9, 715-722).

As DNA sequencing techniques using fluorescent dyes as markers have their maximum emission spectra in the visible range, the DNA is subjected to irradiation in the visible spectra, and visible spectra detectors and light sources are used. Generally photomultiplier tubes are used for detection. As a result, these DNA sequencing techniques have several disadvantages including high costs resulting from the high cost of the lasers used to excite the fluorescent markers which typically emit in the visible region of light spectrum and the high noise to signal ratio due to the background interferences by biomolecules.

Therefore, there remains a need to develop methods of enhancing the fluorescent signals generated by fluorophores to allow the application of fluorescence technology to a variety of analytical, biomedical and material science fields such as physics, chemistry, environmental monitoring and biotechnology.

Citation or identification of any document in this application is not an admission that such a document is available as prior art to the present invention.

SUMMARY OF THE INVENTION

The present invention provides a composition comprising: a hydrogel particle and a fluorophore; wherein said composition produces an enhanced fluorescent signal when excited by an energy source capable of exciting the fluorophore.

The invention further provides a method for making a composition comprising the step of: combining a fluorophore and hydrogel particles; wherein said method generates a composition that produces an enhanced fluorescent signal when excited by an energy source capable of exciting the fluorophore.

In a further aspect, the invention provides a method for making a composition comprising the step of: conjugating a fluorophore to a hydrogel particle; wherein said method generates a composition that produces an enhanced fluorescent signal when excited by an energy source capable of exciting the fluorophore.

In another aspect, the present invention provides a method for enhancing a fluorescence signal comprising the steps of: (a) positioning a fluorophore proximal to a hydrogel particle and (b) exposing the fluorophore-hydrogel particle combination to an energy source capable of exciting the fluorophore.

In another aspect of the present invention a method is provided for detecting or measuring the presence of a fluorophore comprising the steps of: (a) bringing said fluorophore into proximity with a hydrogel particle, (b) exposing the fluorophore and the hydrogel particle to an energy source that is capable of exciting the fluorophore and (c) detecting a fluorescent emission.

There is provided by the present invention an apparatus for detecting or measuring the presence of a fluorophore in a sample, wherein the apparatus comprises: hydrogel particles, a fluorophore, a substrate and an energy source capable of exciting the fluorophore.

The present invention also provides a method for identifying nucleic acids, the method including the steps of: (a) positioning a nucleic acid bound to a fluorophore in proximity to a hydrogel particle, (b) exposing the nucleic acid-fluorophore combination to an energy source capable of exciting the fluorophore, (c) detecting the fluorescence emission, and (d) identifying the nucleic acid based on the fluorescence emission.

In another embodiment, the present invention provides a method for identifying nucleic acids, the method including the steps of: (a) positioning a nucleic acid in proximity to a hydrogel particle, (b) exposing the nucleic acid to an energy source capable of exciting the fluorescence of the nucleic acid, (c) detecting the fluorescence emission from the nucleic acid, and (d) identifying the nucleic acid based on the fluorescence emission.

Still another embodiment provides a method for increasing the fluorescence intensity of a fluorescently labelled biomolecule including the steps of: (a) labelling a biomolecule with a fluorophore, (b) positioning the labelled biomolecule in proximity to a hydrogel particle, (c) exposing the fluorophore-biomolecule combination to an energy source that is capable of exciting the fluorophore and (c) detecting a fluorescent emission.

The present invention also provides a method for increasing the intrinsic fluorescence of a biomolecule including the step of: (a) positioning the intrinsically fluorescent biomolecule in proximity to a hydrogel particle, (b) exposing the biomolecule to an energy source that is capable of exciting the intrinsic fluorescence of the biomolecule and (c) detecting a fluorescent emission.

In another aspect, the present invention provides a composition comprising: hydrogel particles formed into a hydrogel material with environmentally responsive crosslinkages and a fluorophore; wherein said fluorophore-hydrogel particle combination produces an enhanced fluorescent signal when excited by an energy source capable of exciting the fluorophore.

BRIEF DESCRIPTION OF THE DRAWINGS

Comprehension of the invention is facilitated by reading the following detailed description, in conjunction with the annexed drawings.

FIGS. 1a and 1b is a diagrammatic representation of the process of fabricating a hydrogel material with an inbuilt biosensor, whereby the protein or peptide substrates of a target proteolytic enzyme are used to crosslinked to each other and to concentrated pNIPAM-AA particles, forming amide bonds, in the presence of 1-ethyl-3-(3-dimethylaminopropyl)-carbodiimide (EDC).

DISCLOSURE OF THE INVENTION

General

Figure 1C:
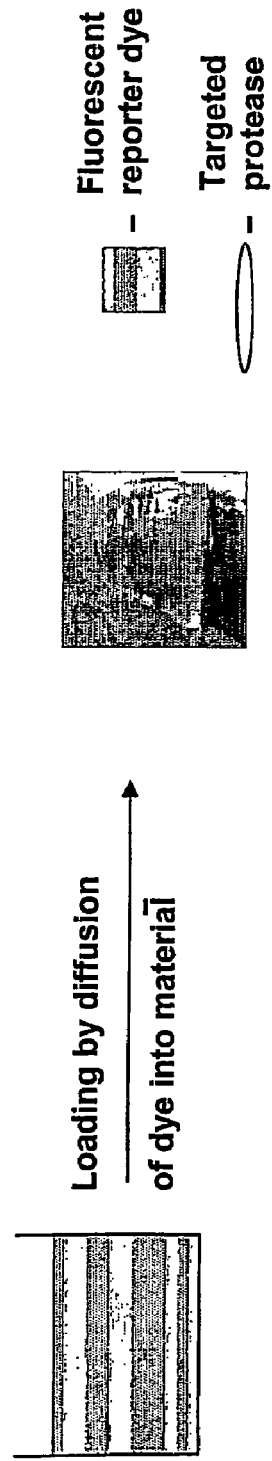
FIG. 1c is a diagrammatic representation of the process of loading a fluorescent compound (ethidium bromide) into a hydrogel material via diffusion. The small picture inset shows a piece of hydrogel material pre-loaded with ethidium bromide.

Those skilled in the art will appreciate that the invention described herein is susceptible to variations and modifications other than those specifically described. The invention includes all such variation and modifications. The invention also includes all of the steps, features, formulations and compounds referred to or indicated in the specification, individually or collectively and any and all combinations or any two or more of the steps or features.

Each document, reference, patent application or patent cited in this text is expressly incorporated herein in their entirety by reference, which means that it should be read and considered by the reader as part of this text. That the document, reference, patent application or patent cited in this text is not repeated in this text is merely for reasons of conciseness.

Any manufacturer's instructions, descriptions, product specifications, and product sheets for any products mentioned herein or in any document incorporated by reference herein, are hereby incorporated herein by reference, and may be employed in the practice of the invention.

The present invention is not to be limited in scope by the specific embodiments described herein, which are intended for the purpose of exemplification only. Functionally equivalent products, formulations and methods are clearly within the scope of the invention as described herein.

The invention described herein may include one or more range of values (eg size, concentration etc). A range of values will be understood to include all values within the range, including the values defining the range, and values adjacent to the range which lead to the same or substantially the same outcome as the values immediately adjacent to that value which defines the boundary to the range.

Throughout this specification, unless the context requires otherwise, the word "comprise" or variations such as "comprises" or "comprising", will be understood to imply the inclusion of a stated integer or group of integers but not the exclusion of any other integer or group of integers. It is also noted that in this disclosure and particularly in the claims and/or paragraphs, terms such as "comprises", "comprised", "comprising" and the like can have the meaning attributed to it in U.S. Patent law; e.g., they can mean "includes", "included", "including", and the like; and that terms such as "consisting essentially of" and "consists essentially of" have the meaning ascribed to them in U.S. Patent law, e.g., they allow for elements not explicitly recited, but exclude elements that are found in the prior art or that affect a basic or novel characteristic of the invention.

Other definitions for selected terms used herein may be found within the description of the invention and apply throughout. Unless otherwise defined, all other scientific and technical terms used herein have the same meaning as commonly understood to one of ordinary skill in the art to which the invention belongs.

DETAILED DISCLOSURE OF THE INVENTION

The present invention provides a composition comprising: a hydrogel particle and a fluorophore; wherein said composition produces an enhanced fluorescent signal when excited by an energy source capable of exciting the fluorophore.

It has surprisingly been found that the presence of the hydrogel particles in a composition containing a fluorophore enhances the fluorescence signal of the composition when the fluorophore is excited by an energy source capable of exciting the fluorophore. By "enhanced" (or "enhances" or "enhancement") it is meant that the presence of the hydrogel particles, in addition to the fluorophore, in the composition results in the intensity of the fluorescence signal generated by the composition being greater than the intensity of a fluorescence signal derived from a composition comprising the fluorophore and not the hydrogel particle.

A hydrogel is a water-containing polymeric network. The polymers used to prepare hydrogels can be based on a variety of monomer types, such as those based on methacrylic and acrylic ester monomers, acrylamide(methacrylamide) monomers, hyaluronic acid, vinyl alcohol, D,L-Lactide, and N-vinyl-2-pyrrolidone. To form the gel, these monomer classes are typically crosslinked with such crosslinking agents as ethylene dimethacrylate, N,N'-methylenebisacrylamide, methylenebis(4-phenyl isocyanate), ethylene dimethacrylate, divinylbenzene, and allyl methacrylate. Particles can also be formed by coating a hydrogel layer e.g. pNIPAM around a core of metal particles e.g. gold nanoparticle (Kim and Lee (2004), Polymeric Materials: Science and Engineering 90, 637-638) or polymer particle e.g. polystyrene particle (Dingenouts et. al. (1998), Macromolecules 31, 8912-8917). Hydrogel particles can be formed as small units of crosslinked monomers.

The hydrogel particles of the present invention are preferably formed from poly N-isopropyl-acrylamide (pNIPAM). More preferably, the pNIPAM is polymerised with the copolymer hydroxyethyl acrylate to form pNIPAM-co-hydroxyethyl acrylate (pNIPAM-HEA), the copolymer acrylic acid to form pNIPAM-co-acrylic acid (pNIPAM-M) or the copolymer allylamine to form pNIPAM-co-allylamine (pNIPAM-Allylamine). Other unsaturated copolymers, such as unsaturated double bond monomers, may be used to introduce functional groups to the pNIPAM polymer backbone for chemical reactions. Such functional groups include amine, sulfurhydry, hydroxyl and carboxyl functional groups and aromatic ring structures. Preferably, the hydrogel particle is a hydrogel nanoparticle.

In one aspect of the invention, the hydrogel particles form a colloidal suspension in a liquid media. Preferably, the liquid media is chosen from the list comprising water, phosphate buffer saline (PBS), 1× Tris-EDTA and other buffers known to the skilled person. The interaction and stability of hydrogel particles in a variety of buffers can be determined by routine trial and error. Too much salt or extremes in pH can lead to aggregation and/or precipitation of the hydrogel particles and different copolymer types and the amount of the copolymer can affect the stability. However, the appropriate buffer and copolymer combination may be determined by the skilled person using routine and well-known methods.

The hydrogel particles will preferably affect the fluorescent intensity of the fluorophore at temperatures above the lower critical solution temperature (LCST). The LCST is the temperature where the hydrogel particles abruptly switch from being hydrophilic to a hydrophobic structure, resulting in a phase separation. It is well known that, pNIPAM exhibits a LCST of 32° C. in water. pNIPAM copolymers may have different LCST values depending on the co-monomers used.

Whilst not being bound to any particular theory, we suggest that the increase in fluorescence intensity is mediated by the phase transition of pNIPAM-HEA particles. Hydrophobic microenvironment inside the particles above the LCST, may increase the fluorescence intensity of hydrophobic fluorophores, which possessed a higher quantum yield in a hydrophobic solvent compared to water.

The random scattering of light from turbid suspensions of pNIPAM copolymer particles may also play a role in the observed fluorescence enhancement. It was reported that random scattering of fluorescent light from kiton red 620/hydroxypropyl cellulose (HPC)/water mixture, above the LCST of HPC, leads to an increase in fluorescent intensity and random lasing. Linear HPC polymers collapsed into 153-277 nm particles and formed turbid suspension above the LCST. Previous random lasers of this kind were fabricated mainly from dyes and metallic particles [Lawandy et al (1994) Nature 368:436-438; Cao H. (2005) Optics & Photonics News 16:24-29]. Interestingly, the kiton red 620/HPC/water random laser showed a narrowing of the linewidth and fluorescence enhancement by a factor of 6-10 folds, a level comparable to the enhancement provided by the presently exemplified fluorophore-pNIPAM copolymer system.

As used hereinafter the terms "fluorophore", "fluorescent dye", "fluorescer", or "fluorochrome" are used interchangeably and bear equivalent meanings. The term "fluorophore" means any substance capable of fluorescing, that is a substance that emits electromagnetic energy such as light at a certain wavelength (emission wavelength) when the substance is illuminated by radiation of a different wavelength (excitation wavelength). Extrinsic fluorophores refer to fluorophores bound to another substance. Intrinsic fluorophores refer to substances that are fluorophores themselves. Thus a compound of interest may be detected by attaching an extrinsic fluorophore to the compound and exposing the fluorophore-compound combination to an energy source capable of exciting the fluorophore such that the fluorophore emits a fluorescent signal, or exposing an intrinsically fluorescent compound of interest to an energy source capable of exciting the intrinsic fluorophore itself such that it emits a fluorescent signal.

Exemplary extrinsic fluorophores include but are not limited to those listed in the Molecular Probes Catalogue (Invitrogen, CA) which is incorporated by reference herein. Representative fluorophores include but are not limited to Alexa Fluor® 350, Dansyl Chloride (DNS-CI), 5-(iodoacetamida) fluoroscein (5-IAF); fluorescein 5-isothiocyanate (FITC), tetramethylrhodamine 5-(and 6-)isothiocyanate (TRITC), 6-acryloyl-2-dimethylaminonaphthalene (acrylodan), 7-nitrobenzo-2-oxa-1,3,-diazol-4-yl chloride (NBD-CI), ethidium bromide, Lucifer Yellow, 5-carboxyrhodamine 6 G hydrochloride, Lissamine rhodamine B sulfonyl chloride, Texas Red™ sulfonyl chloride, BODIPY™, naphthalamine sulfonic acids including but not limited to 1-anilinonaphthalene-8-sulfonic acid (ANS) and 6-(p-toluidinyl)naphthalene-2-sulfonic acid (TNS), Anthroyl fatty acid, DPH, Parinaric acid, TMA-DPH, Fluorenyl fatty acid, Fluorescein-phosphatidylethanolamine, Texas red-phosphatidylethanolamine, Pyrenyl-phophatidylcholine, Fluorenyl-phosphotidylcholine, Merocyanine 540, 1-(3-sulfonatopropyl)-4-[-β-[2[(di-n-butylamino)-6naphthyl]vinyl]pyridinium betaine (Naphtyl Styryl), 3,3'dipropylthiadicarbocyanine (diS-$C_3$-(5)), 4-(p-dipentyl aminostyryl)-1-methylpyridinium (di-5-ASP), Cy-3 Iodo Acetamide, Cy-5-N-Hydroxysuccinimide, Cy-7-Isothiocyanate, rhodamine 800, IR-125, Thiazole Orange, Azure B, Nile Blue, A1 Phthalocyanine, Oxaxine 1,4',6-diamidino-2-phenylindole (DAPI), Hoechst 33342, TOTO, acridine orange, ethidium homodimer, N(ethoxycarbonylmethyl)-6-methoxyquinolinium (MQAE), Fura-2, Calcium Green, Carboxy SNARF-6, BAPTA, coumarin, phytofluors, Coronene, metal-ligand complexes, various type of quantum dots and green fluorescent protein, yellow fluorescent protein, red fluorescent protein, or mutants and derivates thereof.

For example, the extrinsic fluorophore may be selected from the list comprising ethidium bromide, sybr green 1 and fluorescein.

Representative intrinsic fluorophores include, for example, organic compounds having aromatic ring structures including but not limited to tyrosine, tryptophan, phenylalanine (and proteins and peptides with these amino acids), NADH, NADPH, FAD and vitamins. Additional suitable fluorophores include enzyme-cofactors and lanthanide. Purines, pyrimidines, lipids, fatty acids, nucleic acids, nucleotides, nucleosides, proteins, peptides, DNA, RNA and sugars may also act as intrinsic fluorophores.

The fluorophore may be conjugated to the hydrogel particle. For example, the fluorophore may be linked by chemical bonds to the amine, carboxyl, hydroxyl, sulfurhydryl, and other functional groups found on proteins, peptides, sugar groups, etc., which themselves are then linked to hydrogel particles using similar functional groups or other functional groups. Streptavidin/biotin pairing may also be used to link hydrogel particles with fluorophores. Other methods of conjugating or otherwise linking, either reversibly or non-reversibly, a fluorophore with a hydrogel particle are well know to the skilled person.

The fluorophore may also be associated with the hydrogel particle by the following methods:
(a) Covalent linking to conjugate an extrinsic fluorophore to a hydrogel particle (eg. fluorescein isothiocyanate will react with pNIPAM-allylamine copolymer particles, with the amine group present on allylamine forming a covalent bond with fluorescein).
(b) Carrying the extrinsic fluorescent dyes inside the porous hydrogel particle (eg. pNIPAM particles are porous and fluorophores may be carried inside the particle, with the fluorophore not being covalently linked to the particles. The fluorophore can diffuse out rapidly, once the fluorophore-carrying particle is placed in a solution. As the particles reach their LCST, they excrete their fluorophore load more quickly, leading to a reduction in the particle diameter at its LCST.).

(c) Carrying the fluorophore inside hydrogel material (eg. cross-linking a network of hydrogel particles to form hydrogel material and allowing the fluorophore to diffuse into the material overnight, through a concentration gradient. Since the fluorophore is not covalently attached to the hydrogel material, it will diffuse out upon placing the material into a liquid medium. However, upon encountering degradative enzymes that break down the hydrogel material, fluorophores will diffuse more rapidly from the particles because degraded hydrogel material has a bigger surface area compared to a large piece of hydrogel material.)

Alternatively, fluorophores may be associated with the hydrogel particles using a combination of two or more of the above methods. For example, a fluorophore may be added into the reaction mixture during cross-linking of pNIPAM particles with proteins able to, form crosslinkages in the presence of 1-ethyl-3-(3-dimethylaminopropyl)-carbodiimide (EDC). Depending on the structure and molecular weight of the fluorophore and, the cross-linking chemistry, the fluorophore can become both covalently linked to the hydrogel material and trapped in the intra- and inter-particle space. For example, ethidium bromide molecules have two free amine groups and these can react with carboxyl groups on proteins/peptides and pNIPAM-AA to form covalent amide bonds in the presence of EDC. Not all the ethidium bromide will react to form covalent bonds and some will be physically trapped in the hydrogel particles and the hydrogel material matrix through entanglement.

In a preferred aspect of the invention, there is provided a composition comprising: a hydrogel particle and ethidium bromide; wherein said composition produces an enhanced fluorescent signal when excited by an energy source capable of exciting the ethidium bromide. The hydrogel particle is preferably pNIPAM-HEA or pNIPAM-M.

The invention further provides a method for making a composition comprising the step of: combining a fluorophore and a hydrogel particle; wherein said method generates a composition that produces an enhanced fluorescent signal when excited by an energy source capable of exciting the fluorophore.

In a further aspect, the invention provides a method for making a composition comprising the step of: conjugating a fluorophore to a hydrogel particle; wherein said method generates a composition that produces an enhanced fluorescent signal when excited by an energy source capable of exciting the fluorophore. The conjugation may be reversible or irreversible.

In another aspect, the present invention provides a method for enhancing a fluorescence signal comprising the steps of: (a) positioning a fluorophore proximal to a hydrogel particle and (b) exposing the fluorophore-hydrogel particle combination to an energy source capable of exciting the fluorophore.

By "proximal", "in proximity to" or "proximate", it is meant that the fluorophore and the hydrogel particle are touching, or are near enough to each other to allow the hydrogel particle to enhance the fluorescent signal of the fluorophore when the fluorophore is excited by an energy source capable of exciting the fluorophore.

In one aspect, the fluorophore is touching the hydrogel particle, or is conjugated or bound to the hydrogel particle. The binding or conjugation may be reversible or irreversible. Alternatively, the fluorophore may be bound or incorporated into a hydrogel material. Thus, the fluorophore may be incorporated into the crosslinkages that bond the hydrogel particles into a hydrogel material.

Alternatively, one of the fluorophore or the hydrogel particle may be free and carried in a liquid carrier and the other of the fluorophore or hydrogel particle may be immobilised. In this case, the method also includes the step of: flowing the carrier comprising the free component past the immobilised component. For example, the fluorophore may be flowed passed the immobilised hydrogel particles. To aid in flowing the fluorophore through the apparatus, the fluorophore may be provided in a liquid carrier, such as water, PBS or other suitable solvent.

In one example, the carrier comprising a fluorophore may flow over a two dimensional flat surface coated wholly or in part with hydrogel particles. The two dimensional flat surface may alternatively comprise hydrogel material which may be coated in hydrogel particles.

In another example, the carrier containing a fluorophore flows through a porous three dimensional matrix comprising multiple hydrogel particles. The three dimensional matrix may comprise hydrogel particles embedded within the matrix; or the hydrogel particles may form a film surface within the pores of the matrix. The three dimensional matrix may be constructed from a material such as controlled pore glass, or may be constructed from hydrogel material.

Hydrogel material is formed by crosslinking hydrogel particles to form a three-dimensional network. PEG, and salts such as aluminium acetate [see, for example, U.S. Pat. No. 5,069,908]. A variety of small organic molecules e.g. glutaraldehyde, paraformaldehyde, etc. can also be used to crosslink particles together. Other methods of making hydrogel materials, including various hydrogel particles and a variety of cross-linking agents, are well known to the skilled person.

The cross-linkages can also be generated using compounds such as proteins [see, for example, Kim & Healy (2003) Biomacromolecules 4:1214-1223] and polysaccharides such as dextran [see, for example, Van Djik-Wolthuis et al (1995) Macromolecules 28:6317-6322; De Smedt et al (1995) 28:5082-5088], lipids, fatty acids, lipoproteins, DNA and RNA molecules. Advantageously, using cross-linking materials which are the substrate of enzymes allows the formation of bonds that may be broken down selectively, eg by selective agents such as endoproteases, lipases, endonucleases, etc, which possess sequence specificity. This allows the formation of biosensor hydrogel material.

US Patent Application 20030138490 (Hu et. al.) and U.S. Pat. No. 6,497,903 (Hennink et. al.) provide a further class of cross-linkers that spontaneously degrade in the human body. Such cross-linkers have been used to crosslink hydrogel particles and bulk hydrogel to make drug delivery media. Unlike our invention here, these crosslinkers were not designed to be the target of selective enzymes.

The hydrogel material may be formed of the same hydrogel particles as the hydrogel particles that are enhancing the fluorescent signal, or may be formed, from different hydrogel particles. For example, a porous hydrogel material may be formed of hyaluronic acid units, and the pores of this hydrogel material may be provided with pNIPAM hydrogel particles which enhance the fluorescent signal of the fluorophore.

Hydrogel materials may be formed into three dimensional matrices with pores by adding a porosigen during the manufacture of the hydrogel material from hydrogel particles. Early hydrogel materials with porous structures were generated by polymerizing monomers around a crystalline matrix and subsequently removing the crystalline matrix to produce an interconnected porous polymer network. Since that time, porous hydrogel materials have been prepared using salt, sucrose, and ice crystals as the porosigen. These porous hydrogel materials have been used as membranes for affinity chromatography and as tissue engineering substrates wherein tissues are intended to ingrow into the porous hydrogel network. Examples of these porous hydrogel materials are found in U.S. Pat. No. 6,005,161, U.S. Pat. No. 5,863,551 and U.S. Pat. No. 5,750,585.

In one embodiment, the hydrogel particles and/or hydrogel material is chemically inert and does not bind to the compounds of interest (which are bound the fluorophores or are themselves intrinsically fluorescent) or to intermediates that are bound to the compounds to be detected, for example covalently bound. That is, it is not reactive and not biorecognative (not capable of binding the compound to be detected directly or by means of an intermediate binding molecule).

As previously mentioned, the flat surface or three dimensional matrix may be made from hydrogel material or may be made from some other suitable substance such as glass or silica. For example, silica microchips may be used to form the two dimensional flat surface. In one aspect, there is therefore provided a flat surface, such as a silica microchip, which may be provided with multiple island or spots comprising immobilised hydrogel particles. The fluorophore may then flow past the immobilised hydrogel particles. Alternatively, the flat surface may be coated in a film of hydrogel particles, or a hydrogel material, over which the fluorophore may be passed.

When the two dimensional flat surface or three dimensional matrix is made from hydrogel material, the hydrogel material of the surface or matrix itself may act in a similar manner to the hydrogel particles and enhance the fluorescent signal of fluorophores in proximity to the hydrogel material when the fluorophore is excited by an energy source capable of exciting the fluorophore.

The three dimensional matrix may be a nanoporous matrix, through which species such as intrinsically fluorescent compounds of interest and compounds of interest extrinsically linked to fluorophore tags may flow and be both detected and counted more efficiently. Additionally, the efficiency of single molecule counting as fluorophores flow through the matrix may be improved through the use of nanopores. The ability to quantitatively count single flowing molecules under practical conditions may have many implications for medical diagnostics, the detection of biohazard organisms and new and quicker methods for DNA sequencing.

The three dimensional matrix may have an affinity for specific molecules or may filter molecules according to size. For example, a porous silica matrix may be used for size exclusion or inclusion sensing, based upon the pore sizes of the silica, to detect flowing species through the porous silica.

Porous glasses with known pore size distributions may be purchased from a variety of U.S. companies including Geltech and Corning (Corning's Vycor glasses) (Controlled pore glasses, CPLs). Hydrogel particle films may be deposited on the inside of the pores. As an alternative to using known porous glasses which can be lined with hydrogel particle films or films of fluorophore, a porous glass may be created, where the hydrogel particles or fluorophore are embedded within the Walls of the glass.

Controlled pore glasses are typically densified glasses with a known surface area and pore volume/size. The densification of these porous structures can render them relatively inert to a variety of pH's and solvents. Glasses can be readily purchased with narrow pore size distributions as small as a few angstroms to hundreds of nanometers. In addition, glasses are readily available that have been prefunctionalized for applications such as the chemical affinity of biomolecules and have even been used as catalytic agents and bioreactors.

In another aspect of the present invention a method is provided for detecting or measuring the presence of a fluorophore comprising the steps of: (a) bringing said fluorophore into proximity with a hydrogel particle, (b) exposing the fluorophore and the hydrogel particle to an energy source that is capable of exciting the fluorophore and (c) detecting a fluorescent emission.

In a further aspect of the present invention a method is provided for detecting or measuring the presence of a fluorophore comprising the steps of: (a) flowing said fluorophore over a two dimensional flat surface comprising multiple hydrogel particles, (b) exposing the fluorophore and the hydrogel particles to an energy source that is capable of exciting the fluorophore, and (c) detecting a fluorescent emission. The two dimensional flat surface and material structures may be the same as discussed above.

In another aspect of the present invention a method is provided for detecting or measuring the presence of a fluorophore comprising the steps of: (a) flowing said fluorophore through a porous three dimensional matrix comprising multiple hydrogel particles, (b) exposing the fluorophore and the hydrogel particles to an energy source that is capable of exciting the fluorophore, and (c) detecting a fluorescent emission. The three dimensional matrix and material structures may be the same as discussed above.

The method for detecting or measuring the presence of a fluorophore may also be carried out using an immobilised fluorophore and flowing a hydrogel particle over the fluorophore. The two dimensional flat surface and three dimensional matrix and material structures may be the same as discussed above.

There is provided by the present invention an apparatus for detecting or measuring the presence of a fluorophore in a sample, wherein the apparatus comprises: hydrogel particles, a fluorophore, a substrate and an energy source capable of exciting the fluorophore. The substrate may be two dimensional or three dimensional.

Thus, there is provided an apparatus for detecting or measuring the presence of a fluorophore in a sample, wherein the apparatus comprises: hydrogel particles, a fluorophore, a substrate in the form of a two dimensional flat surface and an energy source capable of exciting the fluorophore. The hydrogel particles may be on the surface of the substrate or the surface of the substrate may be formed from hydrogel material.

There is also provided an apparatus for detecting or measuring the presence of a fluorophore in a sample, wherein the apparatus comprises: hydrogel particles, a fluorophore, a porous substrate in the form of a three dimensional matrix and an energy source capable of exciting the fluorophore. The hydrogel particles may be on the surface of the porous substrate or embedded in the porous substrate. The porous substrate may comprise porous silica or porous glass. Alternatively, the apparatus for detecting or measuring the presence of a fluorophore in a sample comprises: a fluorophore, a porous hydrogel material in the form of a three dimensional matrix and an energy source capable of exciting the fluorophore.

Fluorescence can be excited and detected using devices including, but not limited to, a spectrofluorometer having a light source and detector. Light sources can include arc lamps and lasers. Detectors can include photomultiplier tubes. Additionally, it is advantageous for the device to have a monochromator so that specific wavelengths of light may be used to excite a molecule or to detect emissions at a specific wavelength. When a sample containing a fluorophore is placed in the spectrofluorometer and exposed to an amount of exciting energy, the fluorophore emits radiation that is detected by a photomultiplier tube. The fluorescence intensity of a fluorophore can be increased in response to an amount of exciting radiation when the fluorophore is placed near a hydrogel particle.

The present invention also provides a method for identifying nucleic acids, the method including the steps of: (a) positioning a nucleic acid bound to a fluorophore in proximity to a hydrogel particle, (b) exposing the nucleic acid-fluorophore combination to an energy source capable of exciting the fluorophore, (c) detecting the fluorescence emission, and (d) identifying the nucleic acid based on the fluorescence emission.

In another embodiment, the present invention provides a method for identifying nucleic acids, the method including the steps of: (a) positioning a nucleic acid in proximity to a hydrogel particle, (b) exposing the nucleic acid to an energy source capable of exciting the fluorescence of the nucleic acid, (c) detecting the fluorescence emission from the nucleic acid, and (d) identifying the nucleic acid based on the fluorescence emission.

In one embodiment, the background fluorescence is not problematic because the intrinsic fluorescence can be increased by about 5 fold thereby reducing the noise to signal ratio. In another embodiment, the nucleic acid can be identified based on the emission spectra obtained from monitoring the fluorescence of the sample.

Thus, a method is provided of determining the sequence of fluorescently labelled nucleic acids in a sample by the steps of: (a) sequentially removing a fluorescently labelled nucleotide, (b) positioning the nucleotide in proximity to a hydrogel particle, (c) exposing the nucleotide to an energy source capable of exciting the fluorophore, (d) detecting the emitted radiation, and (e) correlating the emitted radiation with the identity of the nucleotide.

A method is also provided for determining the sequence of nucleic acids in a sample by the steps of: (a) sequentially removing a nucleotide, (b) positioning the nucleotide in proximity to a hydrogel particle, (c) exposing the nucleotide to an energy source capable of exciting the fluorescence of the nucleotide, (d) detecting the emitted radiation, and (e) correlating the emitted radiation with the identity of the nucleotide.

Methods for sequentially removing a single nucleotide from a nucleic acid sequence such as an oligonucleotide are known in the art and include sequential digestion, hydrolysis, and chemical cleavage.

The nucleotide can be positioned in proximity to a hydrogel particle by causing the stream of a fluid sample containing a nucleotide to pass near a surface containing the hydrogel particle. The hydrogel particles of such surfaces can be thin films or islands of hydrogel particles that form part of a sample chamber. The exposure of the nucleotide to exciting energy (such as a source of irradiation) can be timed to coincide with the positioning of the nucleotide adjacent to the hydrogel particle. The nucleotide can be exposed to a source of irradiation with one or more wavelengths. In a preferred embodiment, the nucleotides are excited at wavelengths below 300 nm, preferably from 280 to about 295 nm. In another embodiment, the excitation wavelength is near 520 nm for multi-photon excitation.

Still another embodiment provides a method for increasing the fluorescence intensity of a fluorescently labelled biomolecule including the steps of: (a) labelling a biomolecule with a fluorophore, (b) positioning the labelled biomolecule in proximity to a hydrogel particle, (c) exposing the fluorophore-biomolecule combination to an energy source that is capable of exciting the fluorophore and (c) detecting a fluorescent emission.

The present invention also provides a method for increasing the intrinsic fluorescence of a biomolecule including the step of: (a) positioning the intrinsically fluorescent biomolecule in proximity to a hydrogel particle, (b) exposing the biomolecule to an energy source that is capable of exciting the intrinsic fluorescence of the biomolecule and (c) detecting a fluorescent emission.

It will be appreciated that the present invention includes positioning of a biomolecule adjacent to a hydrogel particle or positioning a hydrogel particle adjacent to biomolecule in any of the disclosed embodiments.

The term "biomolecule" means any carbon based molecule occurring in nature or a derivative of such a molecule. The biomolecule can be in active or inactive form. "Active form" means the biomolecule is in a form that can perform a biological function. "Inactive form" means the biomolecule must be processed either naturally or synthetically before the biomolecule can perform a biological function. Exemplary biomolecules include nucleic acids, aromatic carbon ring structures, NADH, FAD, amino acids, carbohydrates, steroids, flavins, proteins, DNA, RNA, oligonucleotides, peptide nucleic acids, fatty acids, sugar groups such as glucose etc., vitamins, cofactors, purines, pyrimidines, formycin, lipids, phytochrome, phytofluor, peptides, lipids, antibodies and phycobiliprotein.

In another aspect, the present invention provides a composition comprising: hydrogel particles formed into a hydrogel material with environmentally responsive crosslinkages and a fluorophore; wherein said fluorophore-hydrogel particle combination produces an enhanced fluorescent signal when excited by an energy source capable of exciting the fluorophore.

By environmentally responsive, it is meant that the crosslinks respond to an environmental factor by changing their nature eg by contracting or expanding or degrading. The environmental factor may be one or more of a variety of factors, such as temperature, chemicals, enzymes etc. Preferably, the environmentally responsive crosslinks are biodegradable ie are degraded by microbial action or by enzymatic action.

Figure 1D:
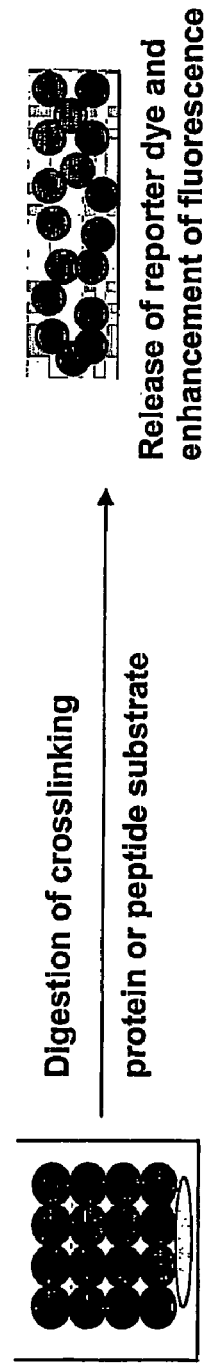
FIG. 1d is a diagrammatic representation of the process of digesting a hydrogel material preloaded with a fluorescent compound (ethidium bromide) using a target protease, resulting in the release of reporter fluorophore and pNIPAM-AA particles which can then be detected.

The fluorophore may be loaded into the hydrogel material by combining the fluorophore with the hydrogel particles prior to crosslinking to form hydrogel material, diffusion or some other suitable method. Alternatively, the fluorophore may be incorporated into the crosslinkages that bond the hydrogel particles into hydrogel material. Thus, when the crosslinkages are degraded, the fluorophore is released along with free hydrogel particles. The presence of hydrogel particles will then result in enhancement of the fluorescent signal of the fluorophore when the fluorophore is exposed to an energy source capable of exciting the fluorophore. FIG. 1 is a diagrammatic representation of the process of preparing such a hydrogel material.

The biodegradable crosslinkers may be made from a range of substances such as proteins, carbohydrates, polysaccharides, (eg. dextran) DNA, RNA, lipids, fatty acids, lipoproteins and other biological macromolecules etc. Preferably, the crosslinkers are made from proteins or polypeptides. More preferably, the crosslinkers are made from a protein, peptide or polypeptide that is degradable by an enzyme. For example, the crosslinkers may be made from bovine serum albumin (BSA) which can be degraded by proteinase K or a range of other proteinases.

The compositions, methods and apparatus of the present invention may be used for a range of other applications where fluorescence signal detection is used. For example, detection of low level chemical pollutants may be enhanced by tagging the pollutant with a fluorophore labelled pollutant specific antibody, which may then be detected as the hydrogel particles enhance the fluorescent signal of the fluorophore to detectable levels. The interaction of fluorophore and hydrogel particles to produce an enhanced fluorescent signal may also be used to increase the fluorescent signal intensity in applications such as microchip assays (eg microarray chips for sequencing, hybridisation etc), sequencing reactions (eg real-time sequencing) and tagging of compounds and molecules of interest (eg tagging surface markers of cells, chromosomal painting etc). Other applications include use as environmental sensors, for toxins that have enzymatic activities e.g. botulinum toxin (botox) or ricin using crosslinked hydrogels that are responsive to these toxin, by degrading or altering their structure such that the fluorophore is released and the fluorescent signal of the fluorophore increased by the presence of hydrogel particles when the fluorophore is exposed to an energy source capable of exciting the fluorophore. Some environmental toxins by nature are fluorescent e.g. aflatoxins, a liver cancer causing toxin is intrinsically fluorescent. Likewise, sensors for detecting residual pollutants post-decontamination, sensors and indicators for diagnostic purposes and means for monitoring chemical reactions in a variety of settings are also contemplated.

Other applications for the present invention include applications that use antibody-antigen interactions, e.g. ELISA, western blotting, immuno-cytochemistry or cell staining. Some of the most sensitive ELISA assays use fluorescence for detection. For example, the alkaline phosphatase substrate, Attophos (Promega), has sensitivities in the attomoles ($10^{-18}$) range and use of the method of the present invention may be able to increase this sensitivity by adding hydrogel particles that can be supplied pre-loaded with the fluorophore. Fluorescence is also utilised in relation to Western Blotting and fluorescent antibodies are commonly used in immuno-cytochemistry applications to locate intracellular and extracellular antigens.

Another potential application of the present technology is to enhance a Real-Time PCR fluorescence signal. Real-Time PCR can detect a single copy of DNA or RNA, but it may takes up to 30 cycles or an hour of amplification before a detectable signal is generated. By combining Real-Time PCR with the fluorescent signal enhancement method of the present invention, it may be possible to make detection faster. Furthermore, other isothermal DNA/RNA amplification and detection technologies such as Strand Displacement Amplification (SDA) and Nucleic Acid Sequence Based Amplification (NASBA) may also benefit from this technology.

The ability to enhance fluorescence and hence signal over noise background may lead to the development of cheaper and more compact PCR machines and other fluorescent detection devices e.g. fluorometers. Currently, most devices used extremely sensitive CCD cameras which are very expensive and big. By enhancing fluorescence detection, the cheaper and smaller, but less sensitive CMOS cameras can be used instead.

The interaction of hydrogel and fluorophore to produce an increased fluorescent signal can also be incorporated into further apparatus, for example a device that can sense the fluorescent signal generated by the degradation of the hydrogel material into particles and release of fluorophore leading to an increased fluorescent signal when the fluorophore is exposed to an source of energy capable of exciting the fluorophore may be used to trigger the release of drugs or chemicals to neutralize toxins, contaminants, etc.

In another application, changes in temperature may be detected by using the present composition of hydrogel particles and fluorophore. When the temperature exceeds the LCST, the structure of the hydrogel particle becomes hydrophobic and intensifies the florescent signal of the fluorophore after exposure to a source of excitation energy. By selecting appropriate hydrogel substance and co-polymer combinations with known LCSTs, changes in temperature can be detected by changes in fluorescence. For example, pNIPAM has a LCST of 32° C. in water. Therefore, it is possible to detect a change in temperature that increases the temperature of a pNIPAM/ethidium bromide solution to greater than 32° C. by measuring the fluorescent signal of the fluorophore. The LCST of a hydrogel particle is affected by a range of factors such as the ionic strength of the suspension solution, the hydrogel chosen, the pH of the solution, and the solvent used to suspend the hydrogel particles.

Hydrogel particles-fluorescent dye mixtures can potentially be turned into random lasers; thereby, increasing the field of applications. Some possible applications for random lasers include brighter pixels on monitors, remote temperature sensors and laser responsive emergency locator which can be displayed by distress boats and be detected by a flying plane using lasers.

The hydrogel materials of the present invention may preferably be used for sense and respond applications. For example, surfaces potentially contaminated with anthrax spores can be overlaid with environmentally responsive hydrogel material loaded with fluorophores and growth media for the spores. Growth media will germinate the spores into bacteria and, as the bacteria increase in numbers, they produce proteases that degrade the environmentally responsive hydrogel material, liberating hydrogel particles and fluorophores. The liberated hydrogel particles and fluorophore can be detected by shining a laser light on it from a great distance, especially if the liberated particles and fluorophore function as a random laser and emit a bright fluorescence that can be recorded by sensors akin to those used in Laser Detection and Ranging (LIDAR) devices. A single spore can grow into a fraction of a colony of bacteria in this manner and can be detected without the need for overnight incubation.

Other applications include "smart" bandages that can detect growth of dangerous bacteria such as cutaneous anthrax and necrotizing fasciitis on wounds. A hydrogel material, generated using environmentally responsive cross-linkages, can be loaded with a fluorophore and incorporated into the bandage, such that growth of the infectious bacteria digests the hydrogel material, releasing the fluorophore and hydrogel particles. As described above, a LIDAR like device can detect the fluorescent signal generated by bacterial growth from a distance. Furthermore, such bandages may also comprise hydrogel material that is preloaded with antibiotics that are released by digestion of the hydrogel material, leading to delivery of antibiotics as the infecting bacteria grows.

A further application of the present technology is the manufacture of food containers incorporating hydrogel material carrying fluorescent edible dyes e.g. curcumin, allura red and erythrosine B. The hydrogel material may be generated with cross-linkages that are degradable in response to common proteases secreted by food poisoning bacteria such as *E. coli, C. botulinum* etc. Such containers can be scanned or illuminated using a LIDAR like device to detect contamination, which will be visible as a fluorescent signal as the fluorescent dye is released from the hydrogel by the contaminating bacteria breaking down the cross-linkages and releasing the fluorophore and the hydrogel particles. Thus, contaminated food can be detected prior to leaving the factory, or can be detected and removed from shop shelves.

EXAMPLES

Further features of the present invention are more fully described in the following non-limiting Examples. It is to be understood, however, that this detailed description is included solely for the purposes of exemplifying the present invention. It should not be understood in any way as a restriction on the broad description of the invention as set out above.

Example 1

Generation of Hydrogel Particles

Temperature sensitive submicron sized hydrogel particles, comprising pNIPAM and copolymer (pNIPAM-HEA and pNIPAM-AA), used in this study were synthesised essentially as described in US Patent Application 20040018160 (Hu et al) with a minor modification. Instead of potassium persulfate, ammonium persulfate was used. The percentage of acrylic acid by weight in the total monomer mixture, including NIPAM, was approximately 2.8%. The concentration of pNIPAM-AA (0.0128 g/ml) and pNIPAM-HEA (0.041 g/ml) particles in water were determined by measuring their freeze dried weight.

Solutions of pNIPAM copolymer particles using PBS as the solvent (rather than water), were generated by freeze drying solutions of pNIPAM in water and then resuspending the dry particles in water and 10×PBS, such that the concentration of pNIPAM copolymer particles in PBS was identical to that in the original water suspension.

Figure 2A:
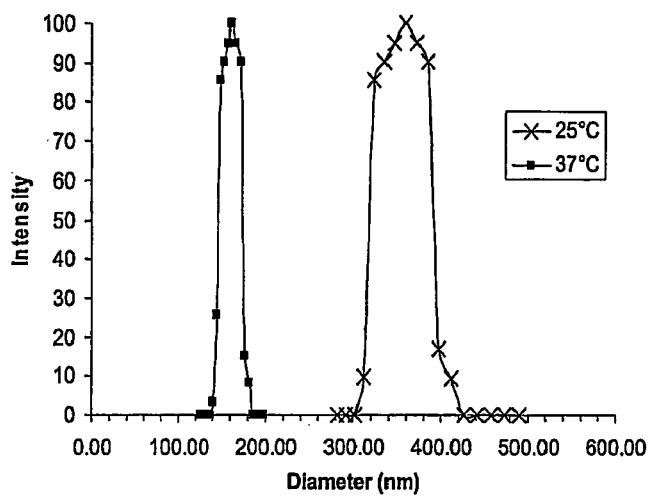
FIG. 2a is a graph showing the particle size of pNIPAM-HEA hydrogel particles suspended in water at various temperatures, measured by dynamic light scattering (DLS).
Figure 2B:
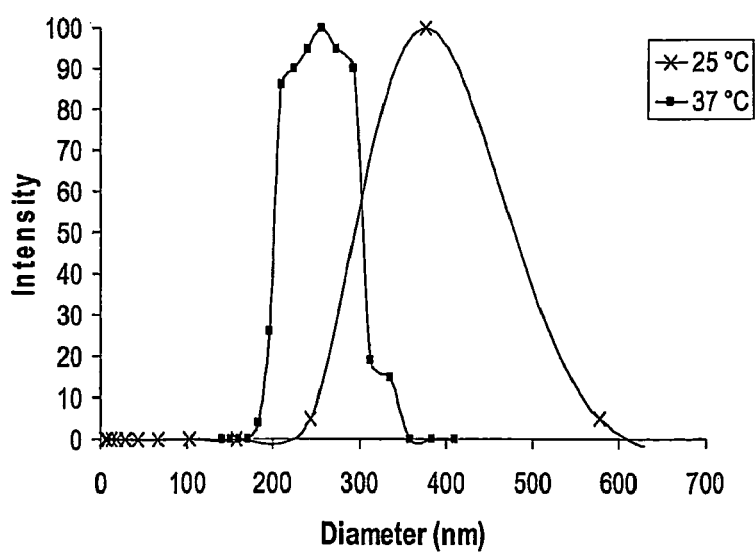
FIG. 2b is a graph showing the particle size of pNIPAM-M hydrogel particles suspended in water at various temperatures, measured by dynamic light scattering (DLS).

FIGS. 2a and 2b show a graph of the particle size at 25° C. and 37° C. of pNIPAM-HEA and pNIPAM-AA hydrogel particles suspended in water. Data on the intensity values G(d) was collected by dynamic light scattering (DLS) using a temperature tunable B1-200SM Research Goniometer System (Brookhaven instruments, NY) and analysed using Brookhaven DLS Software's CONTIN method.

Example 2

Generation of Hydrogel Material

Hydrogel material was synthesised from bovine serum albumin (BSA) and pNIPAM copolymer particles according to the method of Huang et al [Controlled drug release from hydrogel nanoparticle networks. *J Control Release* 94:303-311 (2004); US Patent Appln 20030138490], with some modifications. Briefly, 800 µl of pNIPAM-AA in water was lyophilised and re-suspended in 400 µl water. Then, 40 µl of BSA (0.33 mg/µl) and 60 µl of 1-ethyl-3-(3-dimethylaminopropyl)-carbodiimide(EDC) (10% weight/volume) were added to the particles and mixed rapidly with a pipette. The mixture was incubated overnight at room temperature to allow cross-linking to proceed to completion.

Example 3

Turbidity of Hydrogel Particle Solution in Relation to Temperature

Figure 3:
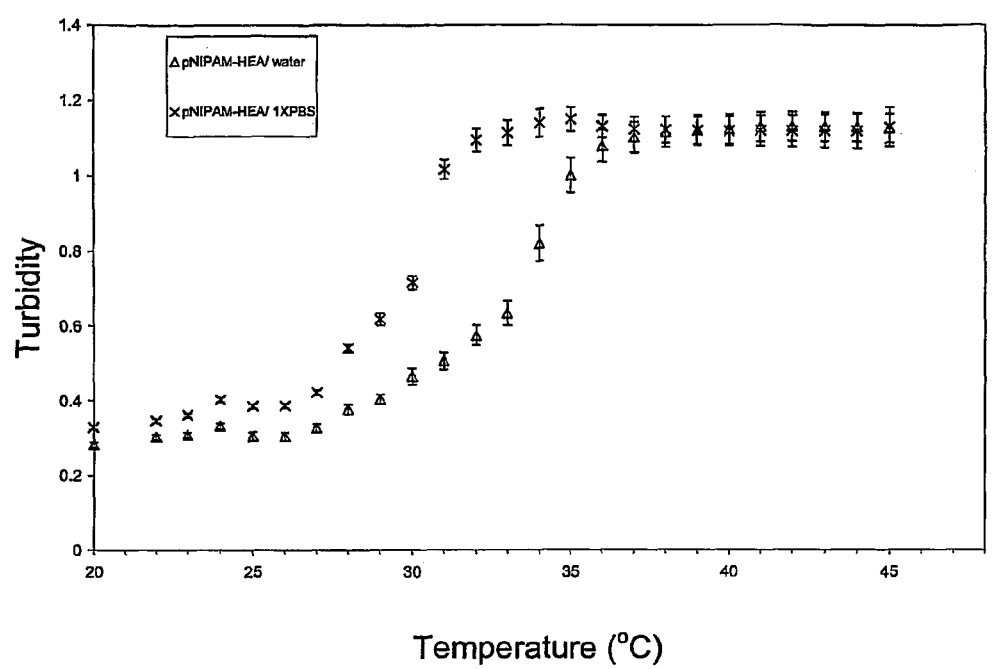
FIG. 3 is a graph showing the changes with temperature in turbidity of pNIPAM-HEA particles suspended in water or PBS. Samples were prepared in triplicate and error bars represent standard error of the mean.

The turbidity of pNIPAM-HEA particles suspended in water or 1×PBS was assessed at different temperatures. Turbidity was assessed by measuring changes in the transmission of a 500 nm wavelength of light through the suspension [see method of Gao & Hu (2002) Langmuir 18:1360-1367]. Transmittance was measured using a Versamax (Molecular Dynamic, CA) UV-Vis Spectrometer with temperature control, at temperatures from 20° C. to 45° C. The results of these experiments are presented in FIG. 3.

The abrupt increase in the turbidity of the suspensions indicates that the LCST has been reached and the hydrogel particles have become hydrophobic, leading to a phase separation.

Example 4

Effect of Temperature on Ability of Hydrogel Particles to Enhance Fluorescence

Samples of pNIPAM-HEA were suspended in water or 1×PBS and various concentrations of ethidium bromide added. The samples were then incubated at either room temperature (25° C.) or 37° C. to determine the effect of hydrogel particles on fluorescence intensity. Fluorescence intensity was measured with a Spectramax Gemini fluorometer (Molecular Devices, CA) with tunable temperature control, ranging from room temperature to 42° C. Excitation and emission wavelengths were 254 nm and 620 nm respectively for ethidium bromide. The results are presented in FIGS. 4a, 4b and 4c.

Figure 4A:
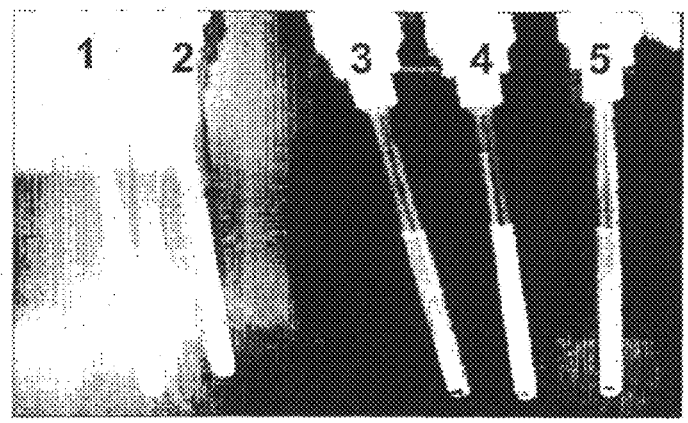
FIG. 4a is a photograph showing the enhancement, by pNIPAM-HEA particles suspended in water, of the fluorescence of 0.1 ug/ul ethidium bromide at 37° C. as observed under UV illumination. Some capillaries were heated to 37° C. on a heat block before photography.

In FIG. 4a, enhancement of ethidium bromide fluorescence in the presence of pNIPAM-HEA particles suspended in water (pNIPAM-HEA/water) at 37° C., can be observed visually. Table 1 shows the contents of the various tubes of FIG. 4a.

TABLE 1

| Sample | Ethidium Bromide | Water | PNIPAM-HEA/water suspension | Temperature |
| --- | --- | --- | --- | --- |
| A | + | + |   | 37° C. |
| B | + |   | + | 37° C. |
| C |   |   | + | Room temp |
| D | + |   | + | Room temp |
| E | + | + |   | Room temp |

Figure 4B:
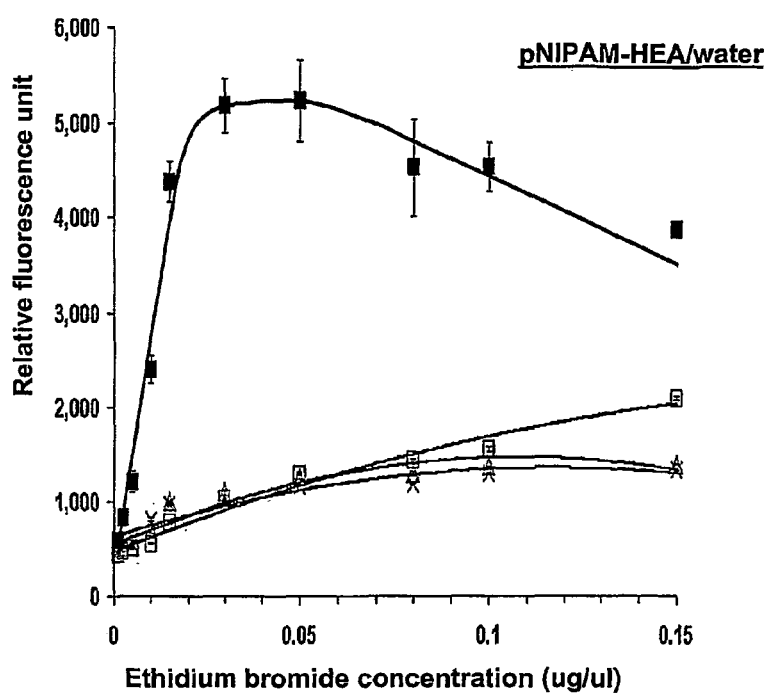
FIG. 4b is a plot of the intensity of ethidium bromide fluorescence at various concentrations in water at 25° C. (Δ) and 37° C. (X), and in pNIPAM-HEA/water suspension at 25° C. (□) and 37° C. (■). Samples were prepared in triplicate and error bars represent standard error of the mean.
Figure 4C:
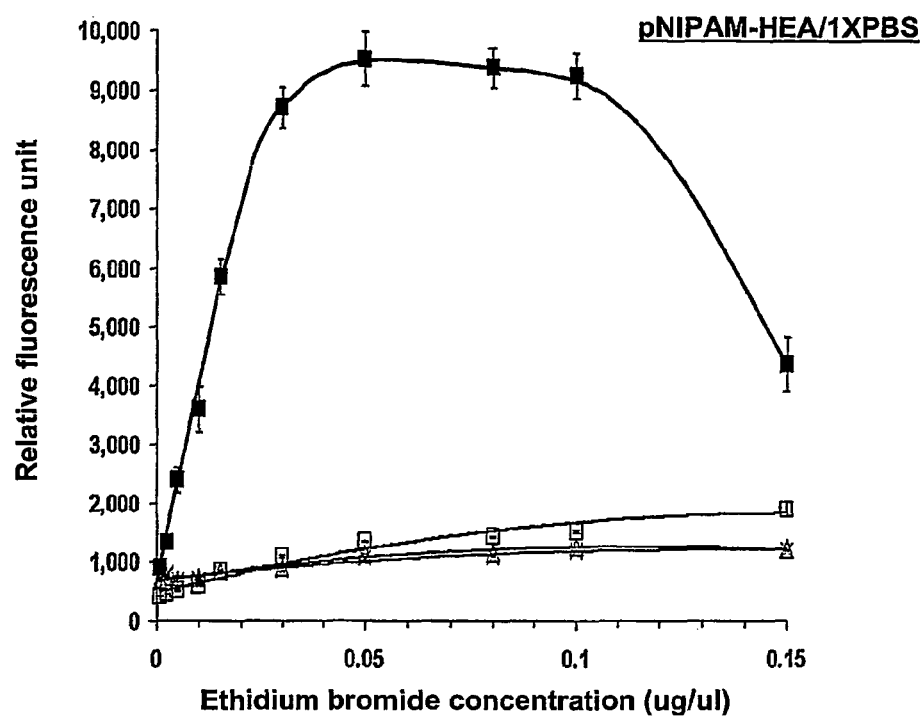
FIG. 4c is a plot of the intensity of ethidium bromide fluorescence at various concentrations in 1×PBS at 25° C. (Δ) and 37° C. (X), and in pNIPAM-HEA/1×PBS suspension at 25° C. (□) and 37° C. (■). Samples were prepared in triplicate and error bars represent standard error of the mean.

FIGS. 4b and 4c presented plots of fluorescence intensity versus ethidium bromide concentrations. The fluorophore was mixed with either water alone or with a suspension of pNIPAM-HEA particles in water (pNIPAM-HEA/water), and with 1× phosphate buffer saline, pH 7.4 (1×PBS) or with a suspension of pNIPAM-HEA particles in 1×PBS (pNIPAM-HEA/1×PBS). Comparing the fluorescence intensities of the fluorophore-pNIPAM-HEA/water mixture between 37° C. and 25° C., a maximum increase of approximately 5 folds can be observed when 0.05 µg/µl of ethidium bromide was used. Similarly, pNIPAM/1×PBS enhanced ethidium bromide fluorescence intensity up to a maximum of approximately 9 folds, when 0.08 µg/µl of ethidium bromide was used.

Example 5

Effect of Temperature on Ability of Hydrogel Particles to Enhance Fluorescence

To determine whether the fluorescence enhancement effect is applicable to other fluorophores, further experiments were performed using sybr green 1 and fluorescein. Excitation and emission wavelengths were 497 nm and 520 nm respectively for sybr green 1, and 494 nm and 518 nm respectively for fluorescein. Plasmid DNA was pGEM-3Z (approximately 2.7 kb) with an insert of approximately 0.4 kb. Assessment of fluorescence was performed as described in Example 4.

Figure 5:
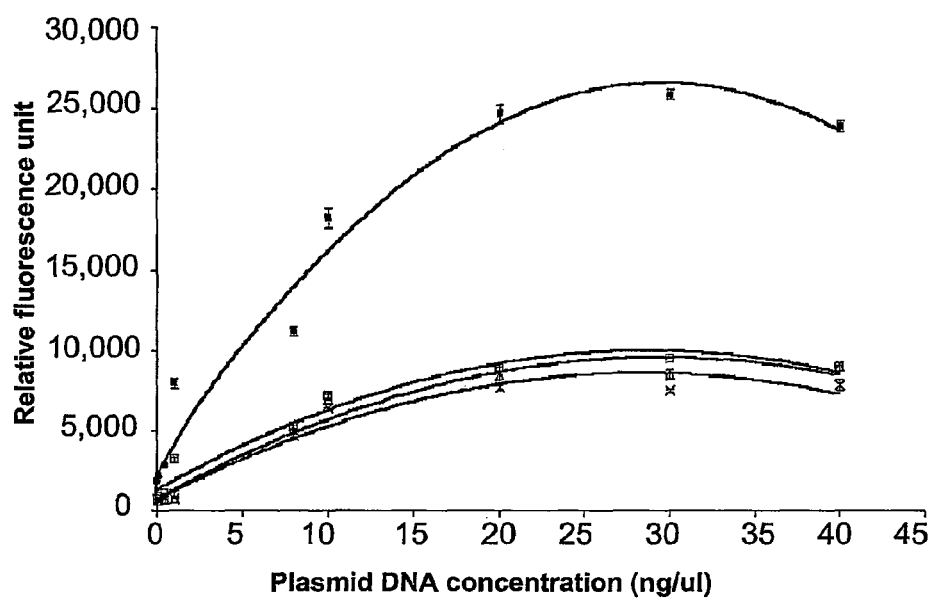
FIG. 5 is a plot of the intensity of Sybr Green 1 fluorescence in the presence of various concentrations of plasmid DNA, in water alone at 25° C. (Δ) and 37° C. (X), and in pNIPAM-HEA/water suspension at 25° C. (□) and 37° C. (■). Samples were prepared in triplicate and error bars represent standard error of the mean.

Sybr green 1 is a fluorophore used in real-time PCR to detect amplicons. FIG. 5 shows the relative fluorescence intensity of sybr green 1 versus various concentrations of plasmid DNA in the presence of a pNIPAM-HEA/water suspension. The concentration of sybr green 1 was fixed at 3× concentrate, diluted from the commercial 10,000× stock. It can be seen in FIG. 5 that the fluorescent intensity of sybr green 1 in the presence of plasmid DNA was enhanced by pNIPAM-HEA/water suspension at 37° C. compared to 25° C., up to a maximum of approximately 3 folds.

Figure 6:
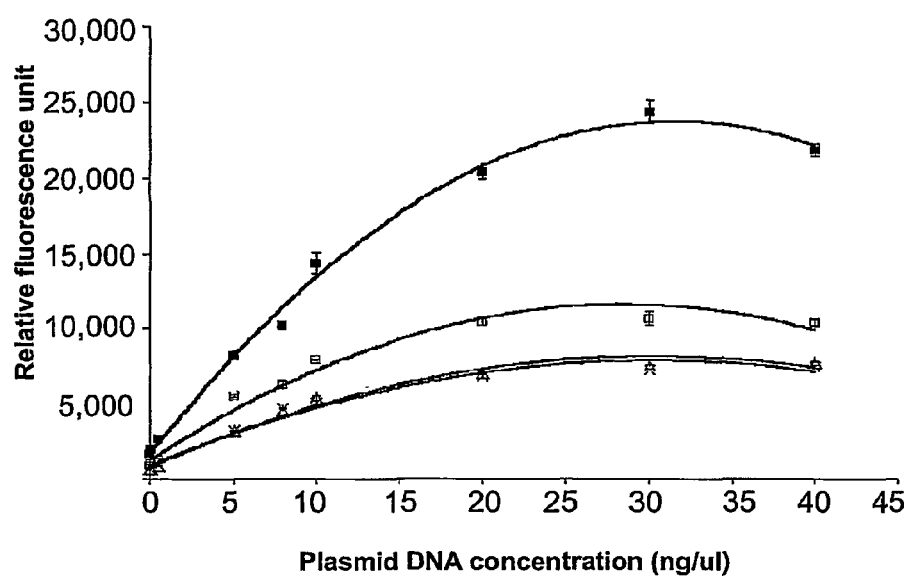
FIG. 6 is a plot of the intensity of Sybr Green 1 fluorescence in the presence of various concentrations of plasmid DNA, in 0.5×PBS alone at 25° C. (Δ) and 37° C. (X), and in pNIPAM-HEA/0.5×PBS suspension at 25° C. (□) and 37° C. (■). Samples were prepared in triplicate and error bars represent standard error of the mean.

In FIG. 6, sybr green 1-plasmid DNA fluorescence was enhanced up to a maximum of approximately 4-5 folds at 37° C., comparing samples with and without pNIPAM-HEA/0.5× PBS.

Figure 7:
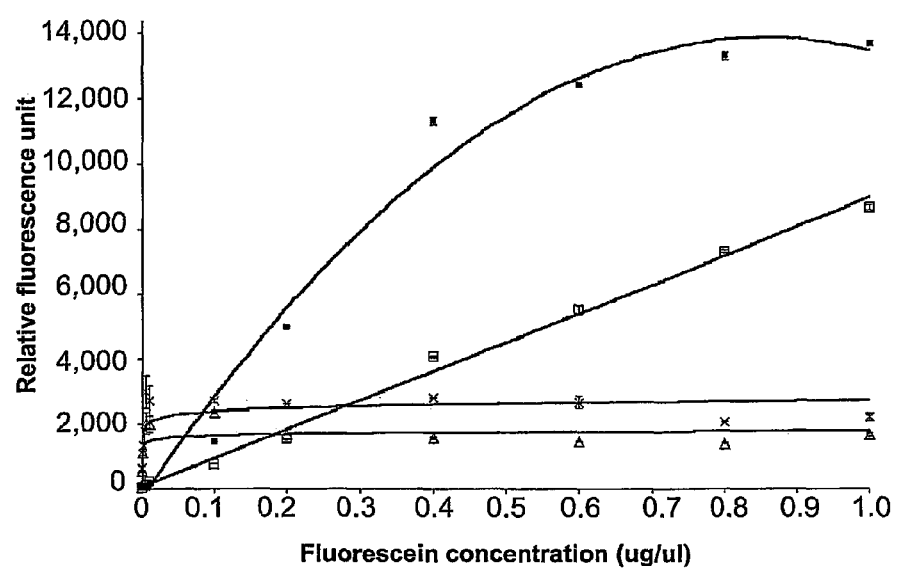
FIG. 7 is a plot of the fluorescence intensity of various fluorescein concentrations in water alone at 25° C. (Δ) and 37° C. (X), and in pNIPAM-HEA/water suspension at 25° C. (□) and 37° C. (■). Samples were prepared in triplicate and error bars represent standard error of the mean.
Figure 8:
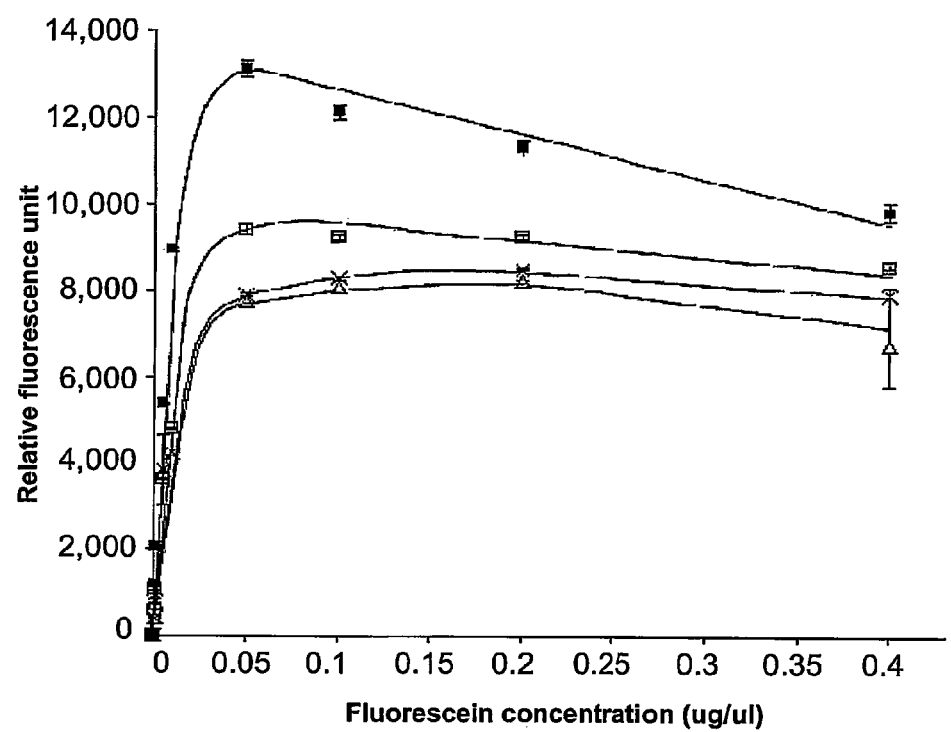
FIG. 8 is a plot of the fluorescence intensity of various fluorescein concentrations in 0.5×PBS alone at 25° C. (Δ) and 37° C. (X), and in pNIPAM-HEA/0.5×PBS suspension at 25° C. (□) and 37° C. (■). Samples were prepared in triplicate and error bars represent standard error of the mean.

Regarding fluorescein, fluorescence intensity was enhanced even at 25° C., when samples with and without pNIPAM-HEA/water suspension were compared at concentration above 0.3 μg/μl fluorescein (FIG. 7). At 37° C., fluorescence enhancement was even greater than 25° C. Interestingly, enhancement of; fluorescence was more subdued when pNIPAM-HEA/0.5×PBS was used (FIG. 8). Comparing samples with and without pNIPAM-HEA/0.5×PBS at 37° C., the sample with particles showed a maximum increase in fluorescence intensity of approximately 0.5 fold, when 0.05 μg/μl fluorescein was used.

Compared to water, higher salt concentration in 0.5×PBS buffer may shield anionic species on fluorescein and disrupt its hydrogen bonding with the hydroxyl group of HEA, suggesting a role played by hydrogen bonding in increasing the fluorescence intensity. Indeed, previous works had shown fluorescein's spectra and quantum yield to be very sensitive to changes in hydrogen bonding with surrounding molecules [Klonis et al (2000) Photochem Photobiol 72:179-185; Klonis et al (1998) Photochem Photobiol 67:500-510; Martin MM (1975) Chem Phys Lett 35:105-111].

Example 6

Preloading Hydrogel Material with Ethidium Bromide

Hydrogel material was washed and equilibrated three times in 1×PBS, each time lasting for 2 hours. Pieces of hydrogel material (approximately 10-30 mg) were dabbed dry with tissue and 1-3 μl of ethidium bromide (10 μg/μl) were placed in contact with the gel for up to 12 hours, to allow diffusion into the gel. The hydrogel was then rinsed once with 1×PBS to remove surface ethidium bromide that had not penetrated the gel, and residual PBS droplets were removed as much as possible.

Fluorophore was also loaded into hydrogel material by adding ethidium bromide, at a final concentration of 0.2 μg/μl, to the hydrogel particle/BSA solution prior to cross-linking to form the hydrogel material (as detailed in Example 2).

Example 7

Assessment of Fluorescence Enhancement Using Pre-Digested Hydrogel Material

Figure 9:
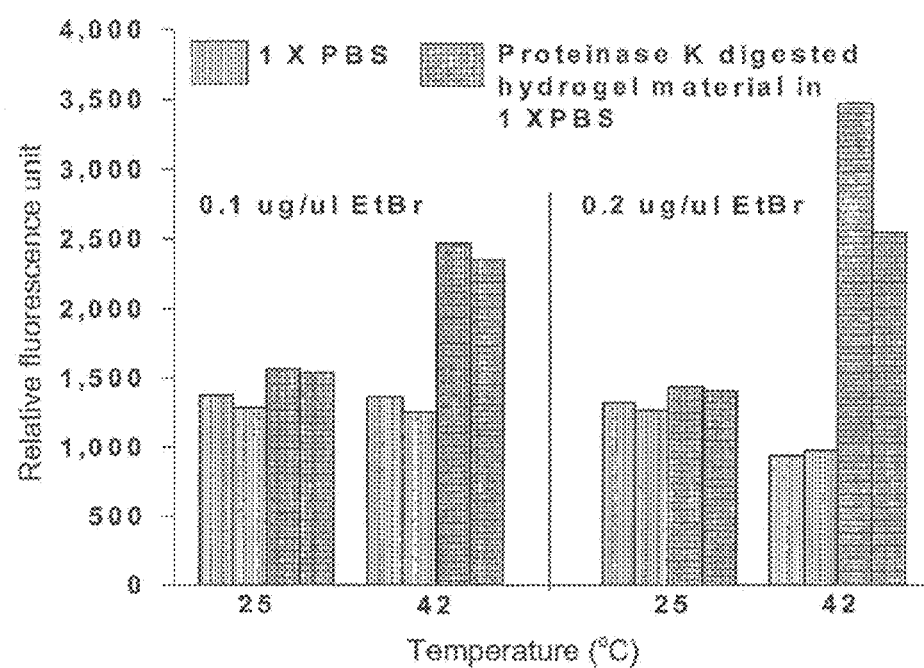
FIG. 9 is a graph showing the relative fluorescence of 0.1 μg/μl and 0.2 μg/μl ethidium bromide in the presence of proteinase K pre-digested hydrogel material at 25° C. and 42° C. Controls are ethidium bromide samples dissolved in 1×PBS, without pre-digested hydrogel material. Experiment is done in duplicates.

To determine the affect of pre-digested hydrogel material on the fluorescence of a fluorophore, 10-30 mg BSA crosslinked hydrogel material was treated with 300 μg of proteinase K in 1×PBS for 2 hours at 37° C. to completely digest the material. The pre-digested hydrogel material was then mixed with ethidium bromide and incubated at 25° C. or 42° C. and the fluorescence measured. Assessment of fluorescence was performed as described in Example 4. The results are presented in FIG. 9.

The fluorescence intensity of ethidium bromide at 0.1 μg/μl and 0.2 μg/μl, with released pNIPAM-AA particles suspended in 1×PBS (pNIPAM-AA/1×PBS) were higher at 42° C. compared to 25° C. A 2.5-3.5 fold increase was observed with 0.2 μg/μl of ethidium bromide in the presence of released pNIPAM-AA/1×PBS compared to ethidium bromide in 1×PBS at 42° C.

Example 8

Assessment of Protease Selectivity

To determine the effect of digestion on the fluorescence of ethidium bromide preloaded into BSA crosslinked hydrogel material, 3 μl of either trypsin (25 μg/1 μl) or proteinase K (100 μg/μl) was added to ~30 mg pre-loaded hydrogel material. The control sample received 3 μl of 1×PBS. The solution was then made up to a volume of 4 μl with 1×PBS and incubated for 120 minutes at 37° C. Undigested intact gel was then separated from the degraded mixture containing hydrogel particles and fluorophores. The mixture was adjusted with 10×PBS to 1×PBS and a volume of 60 μl before readings were done. Assessment of fluorescence was performed as described in Example 4.

Figure 10:
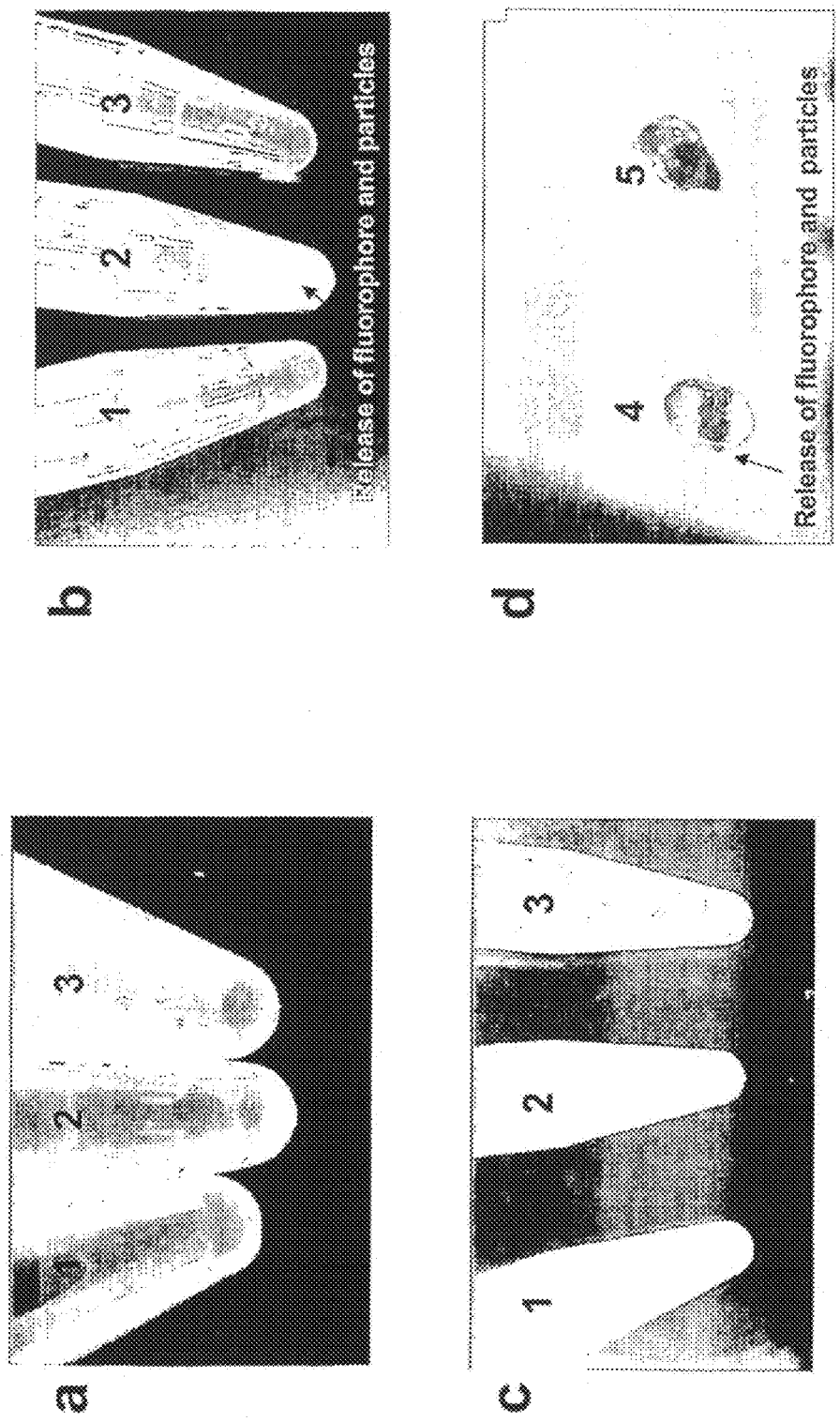
FIG. 10a is a photograph of time=00 samples of hydrogel material, pre-loaded with ethidium bromide, to which either (1) 3 μl of trypsin (25 μg/μl), (2) 3 μl of proteinase K (100 μg/μl) or (3) 3 μl of 1×PBS has been added.
FIG. 10b is a photograph of the samples of FIG. 10a to which 100 μl of 1×PBS has been added after 135 minutes incubation at 37° C.
FIG. 10c is a photograph of the samples of FIG. 10b viewed under UV illumination, after pre-heating to 42° C. for 5-10 minutes.
FIG. 10d is a photograph of a flat petri-dish surface overlaid with hydrogel material, pre-loaded with ethidium bromide, to which droplets of either (4) 1 μl proteinase K (100 μg/μl) or (5) 2 μl of lysozyme (50 μg/μl) have been added and incubated for 135 minutes at 37° C., with the addition of 10 μl of 1×PBS.

The sample is show at time=0 in FIG. 10a, with little fluorescence visible. From FIG. 10b, it can be seen that complete degradation of the hydrogel material was observed with proteinase K, but not trypsin nor 1×PBS, with the release of trapped ethidium bromide. Under UV illumination, the degraded hydrogel material and ethidium bromide mixture shone brighter compared to intact material (FIG. 10c). Trypsin was unable to digest BSA efficiently, probably because it cannot recognise lysine residues whose side chains have formed amide bonds with the carboxy groups on the particles.

Another experiment was also performed using lysozyme and proteinase K (FIG. 10d), but this time the enzymes were spotted onto a flat surface and then overlaid with the hydrogel material. FIG. 10d is a photograph of a flat petri-dish surface overlaid with hydrogel material, pre-loaded with ethidium bromide, to which droplets of either 1 μl proteinase K (100 μg/μl) or 2 μl of lysozyme (50 μg/μl) have been added and incubated for 135 minutes at 37° C., with the addition of 10 μl of 1×PBS. As expected, proteinase K but not lysozyme caused the hydrogel material to leak more ethidium bromide and degraded particles.

Example 9

Assessment of Protease Selectivity and Enhancement of Fluorescence Signal

To further clarify the effect of digestion on the fluorescence of ethidium bromide preloaded via diffusion into BSA crosslinked hydrogel material, 100 μg of either trypsin (25 μg/μl) or proteinase K (25 μg/μl) were added to ~30 mg hydrogel material pre-loaded with ethidium bromide and incubation carried out as described in Example 8 above. Results are presented in FIG. 11.

Hydrogel material treated with trypsin hardly degraded and showed no appreciable fluorescence enhancement at 42°

C. compared to 25° C. In contrast, the release of ethidium bromide and pNIPAM-AA particles after proteinase K treatment led to an approximately 2 fold increase in fluorescence intensity when the temperature was increased from 25° C. to 42° C. Proteinase K digestion completely degraded the hydrogel material and released all the fluorophore.

Figure 12:
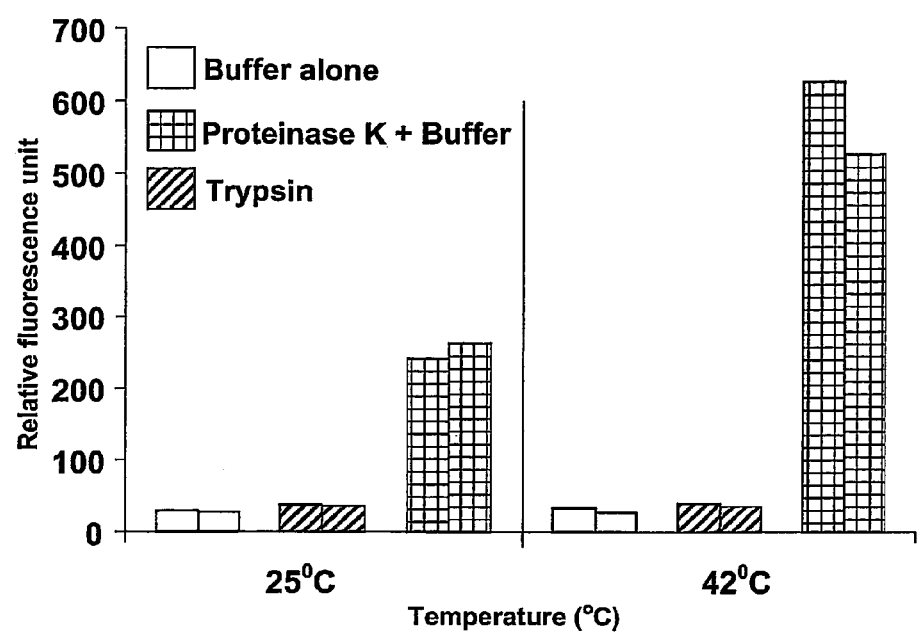
FIG. 12 is a graph showing protease selectivity and the enhancement of fluorescence signal at 25° C. and 42° C., using hydrogel materials with trapped ethidium bromide. Experiment is done in duplicates.

Similar results were found when the experiments were repeated by digesting ~30 mg BSA crosslinked hydrogel material containing trapped ethidium bromide with 100 µg of trypsin (25 µg/µl) or proteinase K (25 µg/µl), or hydrogel material incubated in the presence of buffer alone (FIG. 12). Incubations were carried out according to the method of Example 8.

Example 10

Effect of Serial Dilution

Figure 13:
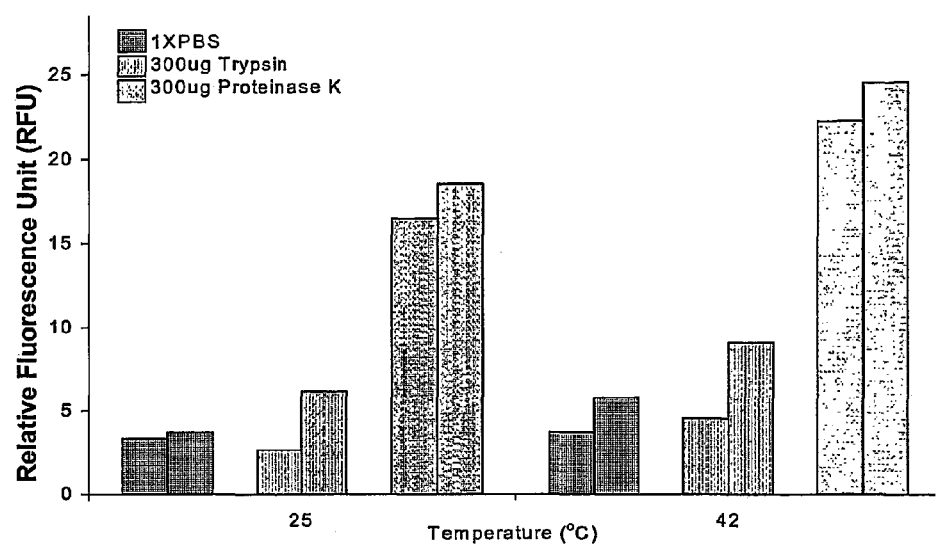
FIG. 13 is a graph showing the degree of self-quenching of fluorescence in samples of hydrogel material pre-loaded with ethidium bromide and digested with protease, by performing a hundred fold dilutions with 1×PBS. Ethidium bromide was pre-loaded into the hydrogel by diffusion. Experiment is done in duplicates.

300 µg of either trypsin (25 µg/µl) or proteinase K (100 µg/µl) were added to ~30 mg hydrogel material pre-loaded with ethidium bromide by diffusion. The mixture was then made up to a volume of 12 µl with 1×PBS, and incubated for 120 minutes at 37° C. As a control, ~30 mg pre-loaded hydrogel was treated with 12 µl of I×PBS. 1 µl of degraded materials were removed and serially diluted with 100 µl of 1×PBS before readings were done. Assessment of fluorescence was performed as described in Example 4. The results are presented in FIG. 13.

It may be seen that that after 100 fold dilution, greater fluorescence was present in the proteinase K digested sample compared to the control. We suggest this may be a result of liberated fluorescence being quenched at high ethidium bromide concentration.

Figure 14:
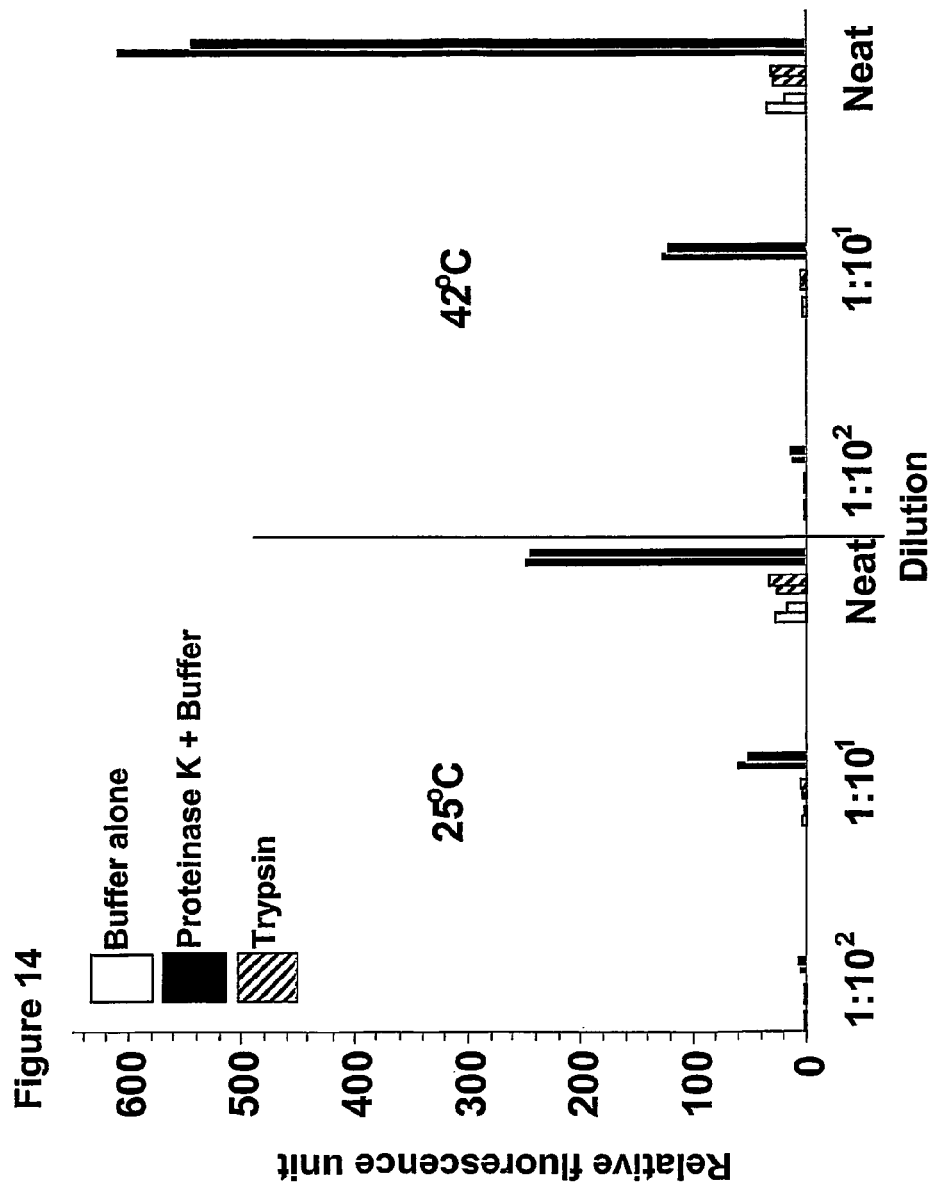
FIG. 14 is a graph showing the ability of ten-fold and one hundred-fold diluted hydrogel material, loaded with trapped ethidium bromide and digested with proteinase K, to enhance fluorescence. Experiment is done in duplicates.

In a further experiment, ~30 mg hydrogel material containing ethidium bromide trapped by crosslinkage into the hydrogel material was treated with either 100 µg of trypsin (25 µg/µl) or proteinase K with buffer (25 µg/µl) or buffer alone for 120 minutes at 37° C. The liberated hydrogel particles/fluorophore mixture was removed and adjusted to 1×PBS. 6 µl of this solution was further diluted 1:10 and then 1:100 with 1×PBS. Assessment of fluorescence was performed as described in Example 4. The results are presented in FIG. 14, where it can be seen that fluorescence enhancement still occurs after a 10 fold dilution in the proteinase K digested sample, probably because the ethidium bromide is trapped with the liberated hydrogel particles.

Figure 11:
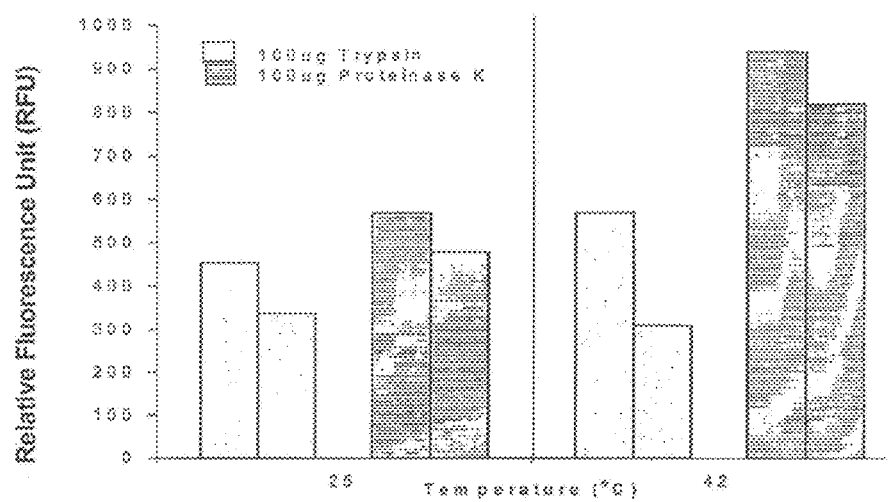
FIG. 11 is a graph showing protease selectivity and the enhancement of fluorescence signal at 25° C. and 42° C., using hydrogel materials pre-loaded with ethidium bromide. Ethidium bromide was pre-loaded into the hydrogel by diffusion. Experiment is done in duplicates.

The fluorescence intensity of the control samples treated with buffer alone or trypsin in FIG. 12 are much lower compared to the fluorescent intensity of control samples in FIG. 11, because ethidium bromide loaded by trapping it in the crosslinkages of the hydrogel matrix does not diffuse out from the hydrogel material into the solution, unlike diffusion loaded hydrogel material in FIG. 11.

Although the invention has been described with reference to certain preferred embodiments, it will be appreciated that many variations and modifications may be made within the scope of the broad principles of the invention. Hence, it is intended that the preferred embodiments and all of such variations and modifications be included within the scope and spirit of the invention, as defined by the following claims.

The claims defining the invention are as follows:

1. A composition comprising: a hydrogel material comprising hydrogel particles crosslinked by enzyme-degradable crosslinkers made from a protein, polysaccharide, peptide or polypeptide and a fluorophore incorporated into the crosslinkages of the hydrogel material, wherein said composition produces an enhanced fluorescent signal when excited by an energy source capable of exciting the fluorophore, wherein the enhanced fluorescent signal generated by the composition of the hydrogel particle and a fluorophore said intensity is greater than the intensity of a fluorescent signal generated by a composition comprising the fluorophore in the absence of the hydrogel particle.

2. The composition of claim 1 wherein the hydrogel particles are formed from poly N-isopropyl-acrylamide (pNIPAM).

3. The composition of claim 2 wherein the pNIPAM is polymerised with hydroxyethyl acrylate to form pNIPAM-co-hydroxyethyl acrylate (pNIPAM-HEA).

4. The composition of claim 2 wherein the pNIPAM is polymerised with acrylic acid to form pNIPAM-co-acrylic acid (pNIPAM-AA).

5. The composition of claim 2 wherein the pNIPAM is polymerised with allylamine to form pNIPAM-co-allylamine acid (pNIPAM-Allylamine).

6. A composition of claim 2 wherein the pNIPAM is polymerised with at least an unsaturated double bond monomer to form a copolymer of pNIPAM which includes functional groups for chemical reactions.

7. A composition of claim 6 wherein the functional group is selected from the group comprising: an amine, a sulfurhydryl, a carboxyl, a hydroxyl, and an aromatic ring structure.

8. The composition of claim 1 wherein the hydrogel particle is a hydrogel nanoparticle.

9. The composition of claim 1 further comprising a liquid media and said composition is a colloidal suspension.

10. The composition of claim 9 wherein the liquid media is chosen from the list comprising: water, phosphate buffer saline (PBS), 1×Tris-EDTA.

11. The composition according to claim 1 wherein the crosslinks are environmentally responsive.

12. The composition according to claim 11 wherein the environmentally responsive crosslinks respond to an environmental factor by contracting, expanding, or degrading.

13. The composition according to claim 12 wherein the environmental factor is selected from the group consisting of temperature, chemical, enzyme, microbial action, enzymatic action, and mixture thereof.

14. The composition according to claim 13 further comprising a growth media for bacterial growth.

15. The composition according to claim 14 wherein the microbial action degrades the hydrogel material, thereby liberating the hydrogel particles and fluorophores.

16. The composition according to claim 1 wherein the crosslinks are bovine serum albumen.

17. The composition according to claim 1 wherein the fluorophore is an extrinsic fluorophore.

18. The composition according to claim 17 wherein the extrinsic fluorophore is selected from the list comprising: Alexa Fluor® 350, Dansyl Chloride (DNS-CI), 5-(iodoacetamida)fluoroscein (5-IAF); fluorescein 5-isothiocyanate (FITC), tetramethylrhodamine 5-(and 6-)isothiocyanate (TRITC), 6-acryloyl-2-dimethylaminonaphthalene (acrylodan), 7-nitrobenzo-2-oxa-1,3,-diazol-4-yl chloride (NBD-CI), ethidium bromide, Lucifer Yellow, 5-carboxyrhodamine 6G hydrochloride, Lissamine rhodamine B sulfonyl chloride, Texas Red™ sulfonyl chloride, BODIPY™, naphthalamine sulfonic acids, 1-anilinonaphthalene-8-sulfonic acid (ANS), 6-(p-toluidinyl)naphthalene-2-sulfonic acid (TNS), Anthroyl fatty acid, DPH, Parinaric acid, TMA-DPH, Fluorenyl fatty acid, Fluorescein-phosphatidylethanolamine, Texas red-phosphatidylethanolamine, Pyrenyl-phophatidylcholine, Fluorenyl-phosphotidylcholine, Merocyanine 540, 1-(3-sulfonatopropyl)-4-[-β-[2-[(di-n-butylamino)-6naphthyl]vinyl] pyridinium betaine (Naphtyl Styryl), 3,3' dipropylthiadicarbocyanine (diS-$C_3$-(5)), 4-(p-dipentyl aminostyryl)-1-methylpyridinium (di-5-ASP), Cy-3 Iodo Acetamide, Cy-5-N-Hydroxysuccinimide, Cy-7-Isothiocyanate, rhodamine 800, IR-125, Thiazole Orange, Azure B, Nile Blue, Al Phthalocyanine, Oxaxine 1,4',6-diamidino-2-phenylindole (DAPI), Hoechst 33342, TOTO, acridine orange, ethidium homodimer, N(ethoxycarbonylmethyl)-6-methoxyquinolinium (MQAE), Fura-2, Calcium Green, Carboxy SNARF-6, BAPTA, coumarin, phytofluors, Coronene, metal-ligand complexes, quantum dots, green fluorescent protein, yellow fluorescent protein, red fluorescent protein, mutants and derivates thereof.

19. The composition according to claim 18 wherein the extrinsic fluorophore is selected from the list comprising: ethidium bromide, Sybr Green 1 and fluorescein.

20. The composition according to claim 1 wherein the fluorophore is an intrinsic fluorophore.

21. The composition according to claim 20 wherein the intrinsic fluorophore is selected from the list comprising: tyrosine, tryptophan, phenylalanine and proteins and peptides with these amino acids, NADH, NADPH, FAD, vitamins, enzyme-cofactors, lanthanide, purines, pyrimidines, lipids, fatty acids, nucleic acids, amino acids, carbohydrates, steroids, flavins, oligonucleotides, aromatic carbon ring structures, nucleotides, nucleosides, proteins, peptides, DNA, RNA, sugars, purines, pyrimidines, formycin, phytochrome, phytofluor, antibodies, phycobiliprotein, and mixture thereof.

22. The composition according to claim 21 wherein the intrinsic fluorophore is a protein.

23. The composition according to claim 1 wherein the fluorophore is conjugated to the hydrogel particle.

24. The composition according to claim 1 wherein the fluorophore is carried inside the hydrogel particle.

25. The composition according to claim 1 wherein the fluorophore is carried inside the hydrogel material.

* * * * *